(12) United States Patent
Valiante

(10) Patent No.: US 8,193,185 B2
(45) Date of Patent: Jun. 5, 2012

(54) USE OF TRYPTANTHRIN COMPOUNDS FOR IMMUNE POTENTIATION

(75) Inventor: Nicholas M. Valiante, Fremont, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 723 days.

(21) Appl. No.: 10/762,873

(22) Filed: Jan. 21, 2004

(65) Prior Publication Data

US 2004/0241192 A1 Dec. 2, 2004

Related U.S. Application Data

(60) Provisional application No. 60/441,641, filed on Jan. 21, 2003.

(51) Int. Cl.
- *A01N 43/58* (2006.01)
- *A01N 43/54* (2006.01)
- *A61K 31/50* (2006.01)
- *C07D 239/42* (2006.01)
- *C07D 401/04* (2006.01)
- *C07D 471/22* (2006.01)
- *C07D 487/04* (2006.01)
- *C07D 471/04* (2006.01)

(52) U.S. Cl. .......... 514/247; 514/256; 514/257

(58) Field of Classification Search .......... 514/247, 514/422, 256, 257
See application file for complete search history.

(56) References Cited

U.S. PATENT DOCUMENTS

| | | | |
|---|---|---|---|
| 4,806,352 A | 2/1989 | Cantrell | 424/282.1 |
| 5,026,543 A | 6/1991 | Riijke | 424/78.31 |
| 5,026,546 A | 6/1991 | Hilgers et al. | 424/280.1 |
| 5,441,955 A | 8/1995 | Baker et al. | 514/250 |
| 6,284,772 B1 | 9/2001 | Pitzer et al. | 514/308 |
| 6,531,487 B2 | 3/2003 | Pitzer et al. | 514/308 |
| 7,122,195 B2 * | 10/2006 | Colston et al. | 424/248.1 |
| 2002/0164341 A1 | 11/2002 | Davis et al. | 424/184.1 |
| 2002/0197269 A1 | 12/2002 | Lingnau et al. | 424/185.1 |

FOREIGN PATENT DOCUMENTS

| | | |
|---|---|---|
| EP | 987027 | 3/2000 |
| WO | WO 98/16247 | 4/1998 |
| WO | WO 98/55495 | 12/1998 |
| WO | WO 03/069303 | 8/2003 |

OTHER PUBLICATIONS

Warren et al., "Current Status of Immunological Adjuvants" *Ann. Rev. Immunol.* 4:369-388, 1986.
O'Hagan et al., "Recent Advantages in the Discovery and Delivery of Vaccine Adjuvants" *Nature Review Discovery* 2:727-735, 2003.
Mitscher et al., "Antimicrobial Agents from Higher Plants . . ." *Heterocycles* 15(2):1017-1019, 1981.
Koya-Miyata et al., Anticancer Research (2001) 21(5):3295-3300.
Micallef et al., International Immunopharmacology (2002) 2(4):565-578.
Scovill et al., Antimicrobial Agents and Chemotherapy (2002) 46(3):882-883.
Sharma et al., Bioorganic and Medicinal Chemistry (2002) 12(17):2303-2307.
Supplementary European Search Report for EP 04704108.2, mailed Aug. 19, 2008, 4 pages.

* cited by examiner

*Primary Examiner* — Yong Chong
(74) *Attorney, Agent, or Firm* — Helen Lee; Otis Littlefield

(57) ABSTRACT

The invention provides immunostimulatory compositions and methods of administration thereof. Also provided are methods of administering a tryptanthrin compound in an effective amount to enhance the immune response of a subject to an antigen. Also provided are methods of administering an effective amount of a tryptanthrin to stimulate the immune response in a subject for the treatment of cancer. Further provided are methods of administering a tryptanthrin compounds as an immunotherapeutic in the treatment of infectious diseases.

7 Claims, 3 Drawing Sheets

USE OF TRYPTANTHRIN COMPOUNDS FOR IMMUNE POTENTIATION

CROSS REFERENCE TO RELATED APPLICATION

This application claims priority to U.S. Provisional Application No. 60/441,641 filed on Jan. 21, 2003, the contents of which are hereby incorporated by reference in its entirety and for all purposes.

FIELD OF THE INVENTION

This invention relates to compounds and compositions, as well as uses of the compounds as immunopotentiators and use of the compounds in methods for treating and preventing viral infections including HCV. More particularly, the invention relates to compounds that are used alone or combined with other agents for which the immune response is desired, in the treatment or modulation of cancer, allergic diseases, asthma, as well as amelioration of viral, bacterial, and fungal infections.

BACKGROUND OF THE INVENTION

Immune response to certain antigens that are otherwise weakly immunogenic can be enhanced through the use of vaccine adjuvants. Such adjuvants potentiate the immune response to specific antigens and are therefore the subject of considerable interest and study within the medical community.

Research has permitted development of vaccines possessing antigenic epitopes that were previously impossible to produce. For example, currently available vaccine candidates include synthetic peptides mimicking streptococcal, gonococcal, and malarial antigens. These purified antigens are generally weak immunogens, however, that require adjuvants in order to evoke protective immunity. However, conventional vaccine adjuvants possess a number of drawbacks that limit their overall use and effectiveness.

Substances that stimulate immune cells in vitro exhibit similar immunostimulatory effects in vivo. These compounds, such as recombinant cytokines, pathogen products (e.g. toxins, lipids, proteins/peptides, carbohydrates and nucleic acids) and other mammalian-derived immunostimulatory molecules (e.g. heat shock proteins, complement, immune complexes and proteoglycans) all induce a measurable pro-inflammatory response both in vitro and in vivo.

Historically, the classic adjuvants have been Freund's complete or incomplete (i.e., without mycobacteria) adjuvants. Edmund Coley described the potential of Coley's toxin for cancer immunotherapy. Other materials, such as mineral oil and aluminum hydroxide, have also been used as adjuvants, but they invariably suffer from disadvantages. For example, mineral oil is known to produce tissue irritation and to be potentially oncogenic. Alum, the only approved adjuvant in the United States, also induces granulomas at the inoculation site and furthermore it does not effectively induce cell-mediated immunity. Moreover, many of the adjuvants currently available have limited utility because they contain components, that are not metabolizable in humans. Additionally, most adjuvants are difficult to prepare in that they may require time consuming procedures and the use, in some cases, of elaborate and expensive equipment to formulate a vaccine and adjuvant system.

Immunological adjuvants are described in "Current Status of Immunological Adjuvants", Ann. Rev. Immunol., 1986, 4, pp. 369-388, and "Recent Advances in Vaccine Adjuvants and Delivery Systems" by Derek T O'Hagan and Nicholas M. Valiente. See also U.S. Pat. Nos. 4,806,352; 5,026,543; and 5,026,546 for disclosures of various vaccine adjuvants appearing in the patent literature.

Immunostimulatory oligonucleotides and polynucleotides are described in PCT WO 98/55495 and PCT WO 98/16247. U.S. Patent Application No. 2002/0164341 describes adjuvants including an unmethylated CpG dinucleotide (CpG ODN) and a non-nucleic acid adjuvant. U.S. Patent Application No. 2002/0197269 describes compositions comprising an antigen, an immunogenic CpG-ODN and a polycationic polymer.

Tryptanthrin (indolo-[2,1-b]quinazolin-6,12-dione) is a material that is produced naturally in some plant species, and has been produced synthetically by a base catalyzed condensation of isatin and isatoic anhydride. Tryptanthrin and some of its analogs have been shown to exhibit some antimicrobial activity against various bacterial and yeast species. Mitscher et al., "Antimicrobial Agents From Higher Plants. New Synthesis and Bioactivity of Tryptanthrin (Indolo-[2,1-b]-quinazolin-6,12-dione) and its Analogs," *Heterocycles* 15(2): 1017-1021 (1981)).

The synthesis of indolo[2,1-b]quinazoline-6,12-dione derivatives and their use in the treatment of pathogenic mycobacterial infections are described in U.S. Pat. No. 5,441,955. U.S. Pat. No. 6,284,772 discloses the use of indolo[2,1-b]quinazoline-6,12-dione derivatives and prodrugs for treatment of malaria.

There has been an effort to find new adjuvants for vaccines that would overcome the drawbacks and deficiencies of conventional adjuvants. In particular, an adjuvant formulation that elicits potent cell-mediated and humoral immune responses to a wide range of antigens in humans and domestic animals, but lacking the side effects of conventional adjuvants, such as Freund's complete adjuvant, would be highly desirable. There also is a need for new small molecule immune potentiators.

SUMMARY OF THE INVENTION

The invention provides novel small molecule immune potentiators (SMIPs), vaccine adjuvant compositions, kits and methods for vaccinating a subject, SMIP pharmaceutical compositions, and methods for stimulating the immune system for the treatment of cancer.

The tryptanthrin compounds used in the methods and compositions of the invention are small molecules that are inexpensive to produce and easy to administer. They have good potential for finer specificity thus providing improved efficacy and safety profiles compared to existing immunostimulants.

As adjuvants, the tryptanthrin compounds may be combined with one or more antigens for use in a delivery system to form a pharmaceutical composition that is a final vaccine product.

As immunotherapeutics, the tryptanthrin compounds are used alone or in combination with other therapies for treatment of chronic infections such as HIV, HCV, HBV, HSV, and *H. pylori*, as well as medicaments for the treatment of cancer.

The tryptanthrin compounds may also be used, for example, for the treatment of BCG, cholera, plague, typhoid, SARS, hepatitis B infection, influenza, inactivated polio, rabies, measles, mumps, rubella, oral polio, yellow fever, tetanus, diphtheria, *hemophilus influenzae* b, meningococcus infection, and pneumococcus infection.

As immunotherapeutics, the tryptanthrin compounds also may be used for the treatment of cancer either alone or in combination with other anti-cancer therapies (e.g. chemotherapeutic agents, mAbs or other immune modulators). The tryptanthrin compounds may be used, for example, for the treatment of BCG, cholera, plague, typhoid, hepatitis B infection, influenza, inactivated polio, rabies, measles, mumps, rubella, oral polio, SARS, yellow fever, tetanus, diphtheria, *hemophilus influenzae* b, meningococcus infection, and pneumococcus infection.

In one embodiment, the tryptanthrin compounds used in the methods, kits, and compositions of the invention are represented by Formula (I):

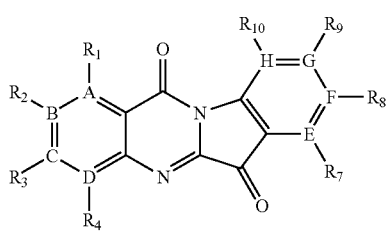

(I)

wherein
A, B, C, D, E, F, G, and H are independently selected from carbon and nitrogen, or A and B and/or C and D can be taken together to be nitrogen or sulfur;

$R_1$, $R_2$, $R_3$, $R_4$, $R_8$, and $R_{10}$ are independently selected from the group consisting of hydrogen, halogen, loweralkyl, alkyl, substituted alkyl, cycloalkyl, heterocyclyl, alkylheterocyclyl, substituted heterocyclyl, substituted alkenyl, amino, (substituted alkyl)(alkyl)amino, imino, haloloweralkyl, hydroxy, alkoxy, substituted alkoxy, hydroxyalkylthio, nitro, alkylsulfonyl, N-alkylsulfonamide, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocyclyl, mercaptoalkoxyalkyl, cyano, formyl, —$COOR_{11}$ wherein $R_{11}$ is hydrogen, loweralkyl, aryl, heterocyclyl, monosaccharide or disaccharide, and —$CONR_{12}R_{13}$ wherein $R_{12}$ and $R_{13}$ are independently selected from hydrogen, loweralkyl, aryl, heterocyclyl, saccharide, peptide and amino acid residues; or $R_2$ and $R_3$ taken together form a six membered aromatic ring;

$R_7$ and $R_9$ are independently selected from hydrogen, halogen, loweralkyl, haloloweralkyl, cycloalkyl, heterocyclyl, substituted heterocyclyl or heterocyclylalkyl; and $R_1$, $R_2$, $R_3$, $R_4$, $R_7$, $R_8$, $R_9$, and $R_{10}$ are absent when the ring atom to which they would otherwise be bonded is sulfur or double-bonded nitrogen; or
a pharmaceutically acceptable salt,
provided that $R_1$, $R_2$, $R_3$, $R_4$, $R_7$, $R_8$, $R_9$, and $R_{10}$ are not all hydrogen when A, B, C, D, E, F, and H are carbon.

In one embodiment, the compounds of Formula (I) have a backbone structure wherein D is nitrogen, and A-C and E-H are carbon.

In one embodiment, when D is carbon, at least one, or at least two of $R_1$-$R_4$, and $R_7$-$R_{10}$ are not hydrogen.

In one embodiment, $R_1$ through $R_4$, and $R_8$ and $R_{10}$ are independently selected from at least two of the group consisting of hydrogen, halogen, loweralkyl, cycloalkyl, heterocyclyl, substituted heterocyclyl, alkylheterocyclyl, amino, imino, haloloweralkyl, alkoxy, nitro, alkylsulfonyl, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocyclyl, mercaptoalkoxyalkyl, cyano, formyl, —$COOR_{11}$ where $R_{11}$ is hydrogen, loweralkyl, aryl, heterocyclyl, monosaccharide or disaccharide, and —$CONR_{12}R_{13}$ where $R_{12}$ and $R_{13}$ are independently selected from hydrogen, loweralkyl, aryl, heterocyclyl, saccharide, peptide and amino acid residues; and $R_4$ is not present when D is nitrogen.

In an additional embodiment, A, B, C, D, E, F, G, and H are independently selected from carbon and nitrogen;

$R_1$, $R_2$, $R_3$, $R_4$, $R_8$ and $R_{10}$ are independently selected from the group consisting of hydrogen, halogen, loweralkyl, alkyl, substituted alkyl, heterocyclyl, substituted heterocyclyl, substituted alkenyl, (substituted alkyl)(alkyl) amino, haloloweralkyl, hydroxy, alkoxy, substituted alkoxy, hydroxyalkylthio, nitro, N-alkylsulfonamide, cyano, —$COOR_{11}$ wherein $R_{11}$ is hydrogen, loweralkyl, aryl, heterocyclyl, monosaccharide or disaccharide, and —$CONR_{12}R_{13}$ wherein $R_{12}$ and $R_{13}$ are independently selected from hydrogen, loweralkyl, aryl, heterocyclyl, saccharide, peptide and amino acid residues.

Provided is a method of enhancing an immune response in a subject to an antigen, the method comprising administering to said subject an antigen and an effective amount of a tryptanthrin compound, or a salt, ester or prodrug thereof, to enhance the immune response to the antigen. The antigen may be derived from a bacterial, parasitic, viral, or fungal pathogen. The immune response is, for example, the cellular production of one or more cytokines.

Also provided is a pharmaceutical composition comprising an antigen and a tryptanthrin compound capable of enhancing an immune response in a host to said antigen. The tryptanthrin compound may be present in a concentration effective to enhance an immune response to an antigen. The composition may further comprise an aqueous carrier.

The tryptanthrin compound used in the methods, kits, and compositions disclosed herein is, for example, a compound of Formula (II):

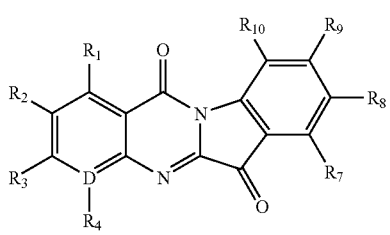

(II)

wherein
D is carbon or nitrogen, and $R_4$ is absent when D is N;
$R_1$ is hydrogen, halogen, or loweralkyl;
$R_2$ is hydrogen or halogen;
$R_3$ is hydrogen, halogen, heterocyclyl, substituted heterocyclyl, (substituted alkyl)(alkyl)amino, or hydroxyalkylthio;
$R_4$ is hydrogen, halogen, alkoxy, substituted alkoxy, or hydroxy;
$R_7$ is hydrogen or haloloweralkyl;
$R_8$ is hydrogen, halogen, substituted alkoxy, haloloweralkyl, nitro, N-alkylsulfonamide, substituted alkenyl, substituted alkyl, $COOR_{11}$ wherein $R_{11}$ is loweralkyl, or —$CONR_{12}R_{13}$ wherein $R_{12}$ and $R_{13}$ are independently hydrogen or loweralkyl;

R₉ is hydrogen; and

R₁₀ is hydrogen, halogen, or loweralkyl;

or a pharmaceutically acceptable salt, ester or prodrug thereof.

The tryptanthrin compound for the methods, kits, and compositions is, for example, one or more compounds selected from the group consisting of:

8-nitroindolo[2,1-b]quinazoline-6,12-dione;
3,8-difluoroindolo[2,1-b]quinazoline-6,12-dione;
10-fluoroindolo[2,1-b]quinazoline-6,12-dione;
1,8-difluoroindolo[2,1-b]quinazoline-6,12-dione;
8-fluoro-1-methylindolo[2,1-b]quinazoline-6,12-dione;
8,10-difluoroindolo[2,1-b]quinazoline-6,12-dione;
2,4-dibromo-1-fluoro-8-iodoindolo[2,1-b]quinazoline-6,12-dione;
2,4-dibromo-1-chloro-8-iodoindolo[2,1-b]quinazoline-6,12-dione;
2,4-dibromo-1-fluoroindolo[2,1-b]quinazoline-6,12-dione;
8-chloro-2-iodoindolo[2,1-b]quinazoline-6,12-dione;
8-chloro-3-fluoroindolo[2,1-b]quinazoline-6,12-dione;
8-fluoro-4-hydroxyindolo[2,1-b]quinazoline-6,12-dione;
N-ethyl-4-(methyloxy)-6,12-dioxo-6,12-dihydroindolo[2,1-b]quinazoline-8-carboxamide;
3-fluoro-8-[(trifluoromethyl)oxy]indolo[2,1-b]quinazoline-6,12-dione;
3-[(2-hydroxyethyl)thio]-8-[(trifluoromethyl)oxy]indolo[2,1-b]quinazoline-6,12-dione;
pyrido[2',3':4,5]pyrimido[1,2-a]indole-5,11-dione;
9-fluoropyrido[2',3':4,5]pyrimido[1,2-a]indole-5,11-dione;
9-bromopyrido[2',3':4,5]pyrimido[1,2-a]indole-5,11-dione;
9-chloropyrido[2',3':4,5]pyrimido[1,2-a]indole-5,11-dione;
9-iodopyrido[2',3':4,5]pyrimido[1,2-a]indole-5,11-dione;
ethyl 5,11-dioxo-5,11-dihydropyrido[2',3':4,5]pyrimido[1,2-a]indole-9-carboxylate;
N-octyl-5,11-dioxo-5,11-dihydropyrido[2',3':4,5]pyrimido[1,2-a]indole-9-sulfonamide;
10-(trifluoromethyl)pyrido[2',3':4,5]pyrimido[1,2-a]indole-5,11-dione;
(5E)-6-(5,11-dioxo-5,11-dihydropyrido[2',3':4,5]pyrimido[1,2-a]indol-9-yl)hex-5-enyl acetate;
6-(5,11-dioxo-5,11-dihydropyrido[2',3':4,5]pyrimido[1,2-a]indol-9-yl)hexyl dihydrogen phosphate; and
9-[(trifluoromethyl)oxy]pyrido[2',3':4,5]pyrimido[1,2-a]indole-5,11-dione;

or a salt, ester or prodrug thereof.

As to the mode of administration of combinations, it should be emphasized that it is the combination of therapeutic agents that gives rise to its synergistic therapeutic effect. The two agents may be given together in a single dose or in separate ones with at the same or a different times and by the same or a different route of administration.

BRIEF DESCRIPTION OF THE TABLES

Table 1 is a list of tryptanthrin compounds and TNF-a activity.

Table 2 is a list of tryptanthrin compounds.

DETAILED DESCRIPTION OF THE INVENTION

Figure 1:
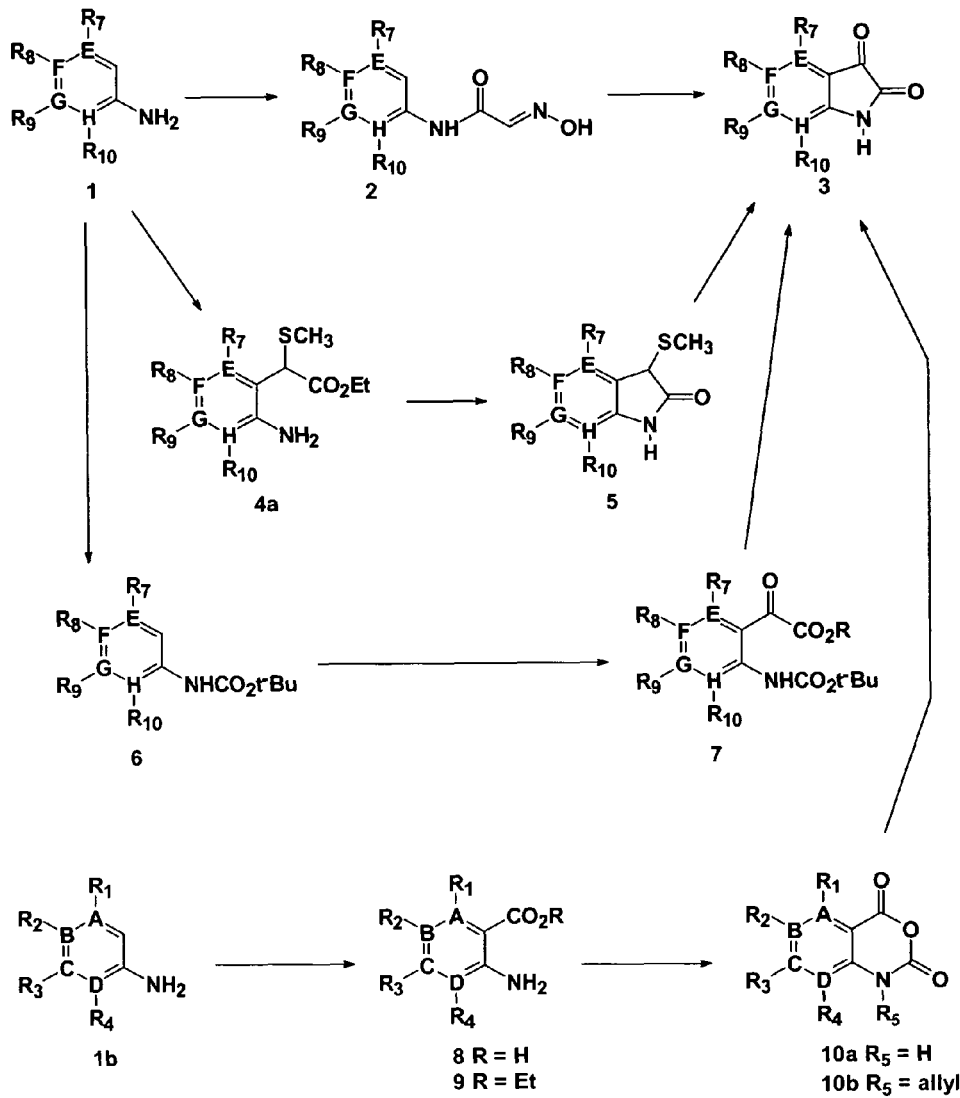
FIG. 1 is a schematic representation of alternative synthesis pathways of intermediate isatin and isatoic anhydride compounds.

As used above and elsewhere herein the following terms and abbreviations have the meanings defined below:

ATP: Adenosine triphosphate
BCG *Mycobacterium bovis bacillus* Calmette-Guerin
BSA: Bovine Serum Albumin
FHA Filamentous haemaglutinin
GCMS Gas Chromatography/Mass Spectroscopy
*H. Pylori Helicobacter Pylori*
HAV Hepatitis A Virus
HBV Hepatitis B Virus
HCV Hepatitis C Virus
HIV Human Immunodeficiency Virus
HPLC High Performance Liquid Chromatography
HSV Herpes Simplex Virus
$IC_{50}$ value: The concentration of an inhibitor that causes a 50% reduction in a measured activity.
IFN Interferon
IL Interleukin
IMS Immunomagnetic separation
IPV Inactivated polio virus
LCMS Liquid Chromatography/Mass Spectroscopy
LPS Lipopolysaccharide
Men A *Neisseria Meningitidis* Type A
Men C *Neisseria Meningitidis* Type C
Men B *Neisseria Meningitidis* Type B
Men W *Neisseria Meningitidis* Type W
Men Y *Neisseria Meningitidis* Type Y
MeOH: Methanol
NANB Non-A, non-B hepatitis
NMR Nuclear magnetic resonance
OMV Outer membrane vesicle
PBMC Peripheral blood mononuclear cells
PT Petussis holotoxin
Rt Room temperature (25° C.)
SARS Severe Accute Respiratory Syndrome
SMIP Small Molecule Immune Potentiator
TLC Thin-layer chromatography
TNF-a Tumour necrosis factor-a The methods of the invention are useful in treating "allergic diseases," which are accomplished in the same way as other immunotherapeutic methods described herein. An "allergen" refers to a substance (antigen) that can induce an allergic or asthmatic response in a susceptible subject. The list of allergens is enormous and can include pollens, insect venoms, animal dander, dust, fungal spores, and drugs (e.g. penicillin).

"Asthma" refers to a disorder of the respiratory system characterized by inflammation, narrowing of the airways and increased reactivity of the airways to inhaled agents. Asthma is frequently, although not exclusively associated with atopic or allergic symptoms.

An "allergen" refers to a substance (antigen) that can induce an allergic or asthmatic response in a susceptible subject. The list of allergens is enormous and can include pollens, insect venoms, animal dander, dust, fungal spores, and drugs (e.g. penicillin).

"Immune-stimulation" or "immune potentiation" refers to activation of the immune system, including humoral or cellular activation, for example, activation of a cell, such as a killer (T or NK) or dendritic cell of the immune system, for example, causing the increase in cytokine production from a dendritic cell leading to an overall enhancement of host defense (immune response).

An "immune-stimulatory effective amount" is an amount effective for activation of the immune system, for example, causing the increase in cytokine production from a dendritic cell leading to an overall enhancement of host defense (immune response).

"Enhancing the immune response to an antigen" by a compound refers to enhancement of the immune response in comparison to that in the absence of the compound. In this embodiment, the compound acts as an adjuvant, for example for use in vaccine compositions and methods.

The term "effective amount" is an amount necessary or sufficient to realize a desired biological effect. For example, an effective amount of a compound to treat an infectious disorder may be an amount necessary to cause an antigen specific immune response upon exposure to an infectious agent. The effective amount may vary, depending, for example, upon the condition treated, weight of the subject and severity of the disease.

As used herein "an effective amount for treatment" refers to an amount sufficient to palliate, ameliorate, stabilize, reverse, slow, delay or prevent progression of a condition such as a disease state.

A "subject" or "patient" is meant to describe a human or vertebrate animal including a dog, cat, horse, cow, pig, sheep, goat, chicken, monkey, rat, and mouse in need of treatment by the methods or compositions of the invention.

As used herein, the term "pharmaceutically acceptable ester" refers to esters, that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

An "immunogenic composition" refers to a composition capable of modulating the production of cytokines in a subject thereby effecting immune potentiation in the subject.

The term "pharmaceutically acceptable prodrugs" as used herein refers to those prodrugs of the compounds of the present invention that are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. Prodrugs as described in U.S. Pat. No. 6,284,772 for example may be used.

The term "acylamino" as used herein refers to an acyl (CO—) radical to which an amino group is appended.

The term "loweralkyl" as used herein refers to branched or straight chain acyclical alkyl groups comprising one to ten carbon atoms, including, e.g., methyl, ethyl, propyl, isopropyl, n-butyl, t-butyl, neopentyl and the like.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following that are provided by way of example: —$CH(CH_3)_2$, —$CH(CH_3)(CH_2CH_3)$, —$CH(CH_2CH_3)_2$, —$C(CH_3)_3$, —$C(CH_2CH_3)_3$, —$CH_2CH(CH_3)_2$, —$CH_2CH(CH_3)(CH_2CH_3)$, —$CH_2CH(CH_2CH_3)_2$, —$CH_2C(CH_3)_3$, —$CH_2C(CH_2CH_3)_3$, —$CH(CH_3)CH(CH_3)(CH_2CH_3)$, —$CH_2CH_2CH(CH_3)_2$, —$CH_2CH_2CH(CH_3)(CH_2CH_3)$, —$CH_2CH_2CH(CH_2CH_3)_2$, —$CH_2CH_2C(CH_3)_3$, —$CH_2CH_2C(CH_2CH_3)_3$, —$CH(CH_3)CH_2CH(CH_3)_2$, —$CH(CH_3)CH(CH_3)CH(CH_3)_2$, —$CH(CH_2CH_3)CH(CH_3)CH(CH_3)(CH_2CH_3)$, and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 3 carbon atoms and include methyl, ethyl, propyl, and —$CH(CH_3)_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; a phosphorus atom in groups such as phosphate and dialkyl alkylphosphonate; oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The term "alkoxy" as used herein refers to RO— wherein R, for example, is alkyl such as loweralkyl defined above. Representative examples of loweralkyl alkoxy groups include methoxy, ethoxy, t-butoxy and the like.

The term "substituted alkoxy" as used herein refers to RO—, where R is, for example, an alkyl substituted, for example, with a halogen. RO is for example $OCF_3$. Another example of substituted alkoxy is arylalkoxy.

The term "alkenyl" as used herein refers to a branched or straight chain groups comprising two to twenty carbon atoms that also comprises one or more carbon-carbon double bonds. Representative alkenyl groups include prenyl, 2-propenyl (i.e., allyl), 3-methyl-2-butenyl, 3,7-dimethyl-2,6-octadienyl, 4,8-dimethyl-3,7-nonadienyl, 3,7,11-trimethyl-2,6,10-dodecatrienyl and the like.

The term "substituted alkenyl" as used herein refers to alkenyl groups that are substituted, for example, diethyl hex-5-enylphosponate, and others with an alkyl or substituted alkyl group such as dialkyl phosphate or an ester such as an acetate ester.

The term "dialkyl amino" as used herein refers to an amino group substituted with two alkyl groups such as C1-20 alkyl groups.

The term "substituted dialkyl amino" as used herein refers to a dialkylamino substituted, for example, with a carboxylic acid, ester, hydroxy or alkoxy.

The term "hydroxyalkylthio" as used herein refers to a thio radical to which is appended a hydroxyalkyl group, where the alkyl is for example lower alkyl. An example is hydroxyethylthio, —$SCH_2CH_2OH$.

The term "N-alkylsulfonamide" as used herein refers to the group —$SO_2NHalkyl$, where alkyl is, for example, octyl.

The term "alkynyl" as used herein refers to a branched or straight chain comprising two to twenty carbon atoms that also comprises one or more carbon-carbon triple bonds. Representative alkynyl groups include ethynyl, 2-propynyl (propargyl), 1-propynyl and the like.

The phrase "aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to aryl groups that substituted alkyl groups had with respect to alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkylaryl" as used herein refers to an arylalkyl group as previously defined appended to an aryl group. Representative arylalkylaryl groups include 4-benzylphenyl, 3-benzylphenyl, 4-phenethylphenyl and the like.

The term "arylaryl" as used herein refers to an aryl group as previously defined that is appended to an aryl group. Representative arylaryl groups include biphenyl, 4-(1-naphthyl)phenyl, 4-(2-naphthyl)phenyl and the like.

The term "aryloxy" as used herein refers to RO— wherein R is an aryl group. Representative arylalkoxy group include benzyloxy, phenylethoxy and the like.

The term "arylalkoxy" as used herein refers to a lower alkoxy radical to which is appended an aryl group. Representative arylalkoxy group include benzyloxy, phenylethoxy and the like.

The term "aryloxyaryl" as used herein refers to an aryl radical to which is appended an aryloxy group. Representative aryloxyaryl groups include 4-phenoxyphenyl, 3-phenoxyphenyl, 4-phenoxy-1-naphthyl, 3-phenoxy-1-naphthyl and the like.

The term "aryloxyarylalkyl" as used herein refers to an arylalkyl radical to which is appended an aryloxy group. Representative aryloxyarylalkyl groups include 4-phenoxyphenylmethyl, 3-phenoxyphenylmethyl, 4-phenoxyphenylethyl, 3-phenoxyphenylethyl and the like.

The term "arylalkoxyaryl" as used herein refers to an aryl radical to which is appended an arylalkoxy group. Representative arylalkoxyaryl groups include 4-benzyloxylphenyl, 3-benzyloxyphenyl and the like.

The term "arylalkoxyarylalkyl" as used herein refers to an arylalkyl radical to which is appended an arylalkoxy group. Representative arylalkoxyarylalkyl groups include 4-benzyloxylbenzyl, 3-benzyloxybenzyl and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl and the like.

The term "halogen" refers to iodine, bromine, chlorine or fluorine; "halo" as used herein refers to iodo, bromo, chloro or fluoro.

The term "haloalkyl" as used herein refers to a lower alkyl radical, as defined above, bearing at least one halogen substituent, for example, chloromethyl, fluoroethyl or trifluoromethyl and the like.

The phrase "heterocyclyl" refers to both aromatic and non-aromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, t-butyloxycarbonyl, and 2-chloropyridyl among others.

"Substituted" refers to the definite replacement of hydrogen with one or more monovalent or divalent radicals. Suitable substitution groups include, those described herein for particular groups, as well as hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

The term "tryptanthrin compound" as used herein includes tryptanthrin (indolo-[2,1-b]quinazolin-6,12-dione) and derivatives thereof. The term "tryptanthrin derivative" as used herein refers to modified forms of tryptanthrin (other than indolo-[2,1-b]quinazolin-6,12-dione itself), modified, for example, by substitution of an atom in one or more of the rings, or by substitution of one or more of the rings with different groups, examples of which are provided herein. Tryptanthrin derivatives and methods for their synthesis are described in U.S. Pat. No. 5,441,955.

The subject invention also includes isotopically-labeled tryptanthrin compounds, that are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds of the present invention, prodrugs thereof, and pharmaceutically acceptable salts of said compounds and of said prodrugs that contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

In accordance with the present invention, methods are provided for the administration of an effective amount of a tryptanthrin compound to act as an adjuvant. Also provided are adjuvant compositions comprising a tryptanthrin compound, an antigen, and optionally other adjuvants.

As adjuvants, the tryptanthrin compounds are combined with one or more antigens and a delivery systems to form a final vaccine product.

As immunotherapeutics, the tryptanthrin compounds are used alone or in combination with other therapies for treatment of chronic viral or bacterial infections such as HIV, HCV, HBV, HSV, SARS, and H. pylori.

In one embodiment, the tryptanthrin compound used in the methods, kits, and compositions disclosed herein is a com pound of Formula (I), or tautomer thereof, or a pharmaceutically acceptable salt, ester, or prodrug thereof:

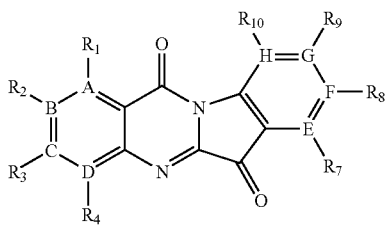

wherein
A, B, C, D, E, F, G, and H are independently selected from carbon and nitrogen, or A and B and/or C and D can be taken together to be nitrogen or sulfur;
$R_1$, $R_2$, $R_3$, $R_4$, $R_8$, and $R_{10}$ are independently selected from the group consisting of hydrogen, halogen, loweralkyl, alkyl, substituted alkyl, cycloalkyl, heterocyclyl, alkylheterocyclyl, substituted heterocyclyl, substituted alkenyl, amino, (substituted alkyl)(alkyl)amino, imino, haloloweralkyl, hydroxy, alkoxy, substituted alkoxy, hydroxyalkylthio, nitro, alkylsulfonyl, N-alkylsulfonamide, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocyclyl, mercaptoalkoxyalkyl, cyano, formyl, —$COOR_{11}$ wherein $R_{11}$ is hydrogen, loweralkyl, aryl, heterocyclyl, monosaccharide or disaccharide, and —$CONR_{12}R_{13}$ wherein $R_{12}$ and $R_{13}$ are independently selected from hydrogen, loweralkyl, aryl, heterocyclyl, saccharide, peptide and amino acid residues; or $R_2$ and $R_3$ taken together form a six membered aromatic ring;
$R_7$ and $R_9$ are independently selected from hydrogen, halogen, loweralkyl, haloloweralkyl, cycloalkyl, heterocyclyl, substituted heterocyclyl or heterocyclylalkyl; and
$R_1$, $R_2$, $R_3$, $R_4$, $R_7$, $R_8$, $R_9$, and $R_{10}$ are absent when the ring atom to which they would otherwise be bonded is sulfur or double-bonded nitrogen; or
a pharmaceutically acceptable salt,
provided that $R_1$, $R_2$, $R_3$, $R_4$, $R_7$, $R_8$, $R_9$, and $R_{10}$ are not all hydrogen when A, B, C, D, E, F, and H are carbon.

In one embodiment of the formulas disclosed herein, D is nitrogen, and $R_4$ is absent.

In one embodiment, when D is carbon, at least one, or at least two of $R_1$-$R_4$ and $R_7$-$R_{10}$ are not hydrogen.

In one embodiment, $R_1$ through $R_4$, and $R_8$ and $R_{10}$ are independently selected from at least two or more of the group consisting of hydrogen, halogen, loweralkyl, cycloalkyl, heterocyclyl, substituted heterocyclyl, alkylheterocyclyl, amino, imino, haloloweralkyl, alkoxy, nitro, alkylsulfonyl, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocyclyl, mercaptoalkoxyalkyl, cyano, formyl, —$COOR_{11}$ where $R_{11}$ is hydrogen, loweralkyl, aryl, heterocyclyl, monosaccharide or disaccharide, and —$CONR_{12}R_{13}$ where $R_{12}$ and $R_{13}$ are independently selected from hydrogen, loweralkyl, aryl, heterocyclyl, saccharide, peptide and amino acid residues; and $R_4$ is not present when D is nitrogen.

In an additional embodiment, A, B, C, D, E, F, G, and H are independently selected from carbon and nitrogen;
$R_1$, $R_2$, $R_3$, $R_4$, $R_8$ and $R_{10}$ are independently selected from the group consisting of hydrogen, halogen, loweralkyl, alkyl, substituted alkyl, heterocyclyl, substituted heterocyclyl, substituted alkenyl, (substituted alkyl)(alkyl) amino, haloloweralkyl, hydroxy, alkoxy, substituted alkoxy, hydroxyalkylthio, nitro, N-alkylsulfonamide, cyano, —$COOR_{11}$ wherein $R_{11}$ is hydrogen, loweralkyl, aryl, heterocyclyl, monosaccharide or disaccharide, and —$CONR_{12}R_{13}$ wherein $R_{12}$ and $R_{13}$ are independently selected from hydrogen, loweralkyl, aryl, heterocyclyl, saccharide, peptide and amino acid residues.

In another embodiment, the tryptanthrin compound for the methods, kits, and compositions is a compound of Formula (II):

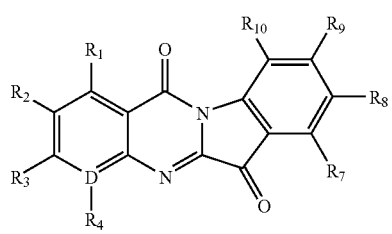

wherein
D is carbon or nitrogen, and $R_4$ is absent when D is N;
$R_1$ is hydrogen, halogen, or loweralkyl;
$R_2$ is hydrogen or halogen;
$R_3$ is hydrogen, halogen, heterocyclyl, substituted heterocyclyl, (substituted alkyl)(alkyl)amino, or hydroxyalkylthio;
$R_4$ is hydrogen, halogen, alkoxy, substituted alkoxy, or hydroxy;
$R_7$ is hydrogen or haloloweralkyl;
$R_8$ is hydrogen, halogen, substituted alkoxy, haloloweralkyl, nitro, N-alkylsulfonamide, substituted alkenyl, substituted alkyl, $COOR_{11}$ wherein $R_{11}$ is loweralkyl, or —$CONR_{12}R_{13}$ wherein $R_{12}$ and $R_{13}$ are independently hydrogen or loweralkyl;
$R_9$ is hydrogen; and
$R_{10}$ is hydrogen, halogen, or loweralkyl;
and pharmaceutically acceptable salts, esters or prodrugs thereof.

In one embodiment, when D is carbon, at least one or at least two of $R_1$-$R_4$, and $R_7$-$R_{10}$ are not hydrogen.

In one embodiment, $R_1$ through $R_4$, and $R_8$ and $R_{10}$ are independently selected from at least two of the group consisting of hydrogen, loweralkyl, heterocyclyl, substituted heterocyclyl, amino, halogen, nitro, alkylamino, dialkylamino, alkoxyalkylamino, and alkylheterocyclyl, provided that $R_4$ is absent when D is N.

In another embodiment, the tryptanthrin compound for the methods, kits, and compositions is a compound of Formula (III):

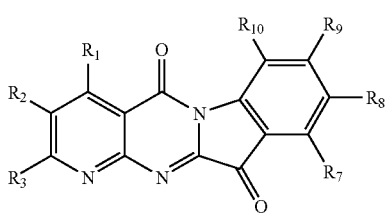

wherein $R_1$ through $R_3$, $R_8$ and $R_{10}$ are independently selected from the group consisting of hydrogen, loweralkyl, heterocyclyl, substituted heterocyclyl, amino, halogen, nitro, alkylamino, dialkylamino, alkoxyalkylamino, and alkylheterocyclyl;

$R_7$ and $R_9$ are independently selected from hydrogen, halogen, loweralkyl, cycloalkyl, heterocyclyl, substituted heterocyclyl and heterocyclicalkyl;

and pharmaceutically acceptable salts, esters and prodrugs thereof.

In another embodiment, the tryptanthrin compound for the methods, kits, and compositions is a compound of Formula (IV):

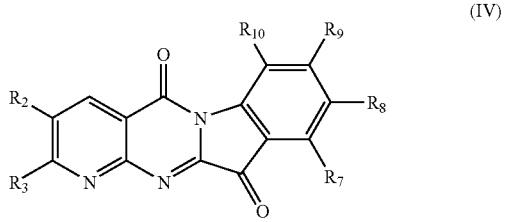

(IV)

wherein $R_2$, $R_3$, $R_8$ and $R_{10}$ are independently selected from the group consisting of hydrogen, halogen, loweralkyl, heterocyclyl, and substituted heterocyclyl;

$R_7$ and $R_9$ are independently selected from hydrogen and halogen;

and pharmaceutically acceptable salts, esters and prodrugs thereof.

In another embodiment, the tryptanthrin compound for the methods, kits, and compositions, is a compound represented by Formula (II):

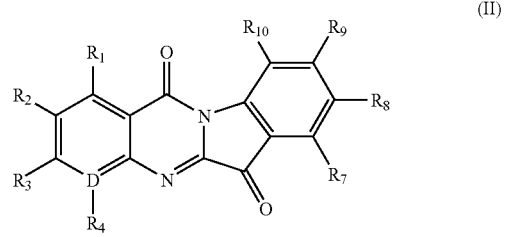

(II)

wherein

D is carbon or nitrogen, and $R_4$ is absent when D is N;
$R_1$ is hydrogen, halogen, or loweralkyl;
$R_2$ is hydrogen or halogen;
$R_3$ is hydrogen, halogen, heterocyclyl, substituted heterocyclyl, substituted dialkylamino, or hydroxyalkylthio;
$R_4$ is hydrogen, halogen, alkoxy or hydroxy;
$R_7$ is hydrogen or haloloweralkyl;
$R_8$ is hydrogen, halogen, substituted alkoxy, haloloweralkyl, nitro, N-alkylsulfonamide, substituted alkenyl, substituted alkyl, $COOR_{11}$ where $R_{11}$ is loweralkyl, or —$CONR_{12}R_{13}$ where $R_{12}$ and $R_{13}$ are independently hydrogen or loweralkyl;
$R_9$ is hydrogen; and
$R_{10}$ is hydrogen, halogen, or loweralkyl;
wherein, in one embodiment, at least one of $R_1$-$R_4$ and $R_7$-$R_{10}$ is not a hydrogen atom;
and pharmaceutically acceptable salts, esters and prodrugs thereof.

In another embodiment, the tryptanthrin compound for the methods, kits, and compositions is a compound of Formula (II) wherein:

D is carbon or nitrogen, and $R_4$ is absent when D is N;
$R_1$ is hydrogen, halogen or loweralkyl;
$R_2$ is hydrogen or halogen;
$R_3$ is hydrogen, halogen, or hydroxyalkylthio;
$R_4$ is hydrogen, halogen, alkoxy or hydroxy;
$R_7$ is hydrogen or haloloweralkyl;
$R_8$ is hydrogen, halogen, substituted alkoxy, haloloweralkyl, nitro, N-alkylsulfonamide, substituted alkenyl, substituted alkyl, $COOR_{11}$ where $R_{11}$ is loweralkyl, or —$CONR_{12}R_{13}$ where $R_{12}$ and $R_{13}$ are independently hydrogen or loweralkyl;
$R_9$ is hydrogen; and
$R_{10}$ is hydrogen, halogen, or loweralkyl;
wherein in one embodiment at least one of $R_1$-$R_4$ and $R_7$-$R_{10}$ is not hydrogen;
and pharmaceutically acceptable salts, esters and prodrugs thereof.

In another embodiment, the tryptanthrin compound for the methods, kits, and compositions is a compound of Formula (II) wherein:

D is carbon or nitrogen, and $R_4$ is absent when D is N;
$R_1$ is hydrogen, halogen, alkyl or loweralkyl;
$R_2$ is hydrogen or halogen;
$R_3$ is hydrogen, halogen, heterocyclyl, substituted heterocyclyl, amino, alkylamino, dialkylamino, substituted dialkylamino, or hydroxyalkylthio;
$R_4$ is hydrogen, halogen, alkoxy or hydroxy;
$R_7$ is hydrogen, alkyl or haloloweralkyl;
$R_8$ is hydrogen, halogen, alkyl, substituted alkoxy, haloloweralkyl, nitro, N-alkylsulfonamide, substituted alkenyl, substituted alkyl, $COOR_{11}$ where $R_{11}$ is loweralkyl, or —$CONR_{12}R_{13}$ where $R_{12}$ and $R_{13}$ are independently hydrogen or loweralkyl;
$R_9$ is hydrogen; and
$R_{10}$ is hydrogen, halogen, or loweralkyl;
wherein in one embodiment at least one of $R_1$-$R_4$ and $R_7$-$R_{10}$ is not hydrogen;
and pharmaceutically acceptable salts, esters and prodrugs thereof.

It should be understood that the organic compounds described herein may exhibit the phenomenon of tautomerism. It should be understood that the invention encompasses any tautomeric form of the drawn structure. The compounds comprise asymmetrically substituted carbon atoms. Such asymmetrically substituted carbon atoms can result in the compounds comprising mixtures of stereoisomers at a particular asymmetrically substituted carbon atom or a single stereoisomer. As a result, racemic mixtures, mixtures of diastereomers, as well as single diastereomers of the compounds are included in the present invention. The terms "S" and "R" configuration, as used herein, are as defined by the IUPAC 1974 *Recommendations for Section E, Fundamental Stereochemistry, Pure Appl. Chem.* (1976) 45, 13-30. The terms α and β are employed for ring positions of cyclic compounds. The α-side of the reference plane is that side on which the preferred substituent lies at the lowered numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the *Chemical Abstracts Index Guide—Appendix IV* (1987) paragraph 203.

One embodiment of the invention is directed to a method of inducing an immunostimulatory effect in a patient comprising administering a tryptanthrin compound in an amount effective to stimulate an immune response such as a cell-mediated immune response.

The tryptanthrin compounds can be used with or without an antigen in therapeutic applications, for example to treat cancer or infectious diseases. The tryptanthrin compounds also may be used in combination with other therapeutic agents, such as anti-virals and monoclonal antibodies in different therapeutic applications.

An embodiment of the method of inducing an immunostimulatory effect in a subject is directed to administering a vaccine adjuvant composition comprising an antigen in an amount effective to stimulate an immune response such as a cell-mediated immune response and, as a vaccine adjuvant, a tryptanthrin compound, in an amount effective to potentiate the immune response such as the cell-mediated immune response to the antigen.

For the method of inducing an immunostimulatory effect in a subject, the antigen and the tryptanthrin compound may be administered at the same or different times and by the same or different routes of administration.

A further embodiment of the invention is a vaccine adjuvant composition comprising one or more tryptanthrin compounds, one or more antigens, and a pharmaceutically acceptable excipient. The vaccine adjuvant composition can further comprise one or more non-tryptanthrin adjuvants.

An embodiment of the invention is a kit for stimulating an immune response in a subject comprising one or more tryptanthrin compounds, one or more antigens, one or more containers, and optionally a delivery device such as a syringe, a nasal inhaler, or a transdermal patch. In the case of the kit embodiment containing a syringe or one or more containers adapted for use with a syringe, the container or containers may contain additional pharmaceutically acceptable excipients. The kit may comprise a first container containing a tryptanthrin adjuvant or adjuvant combination such as an additional tryptanthrin adjuvant or non-tryptanthrin adjuvant and optionally containing an antigen or mixture of antigens. The kit may further comprise a second container that may contain a different antigen or a different mixture of antigens from the first container or the second container may contain a lyophilized antigen composition wherein the intended method of delivery of the contents of the kit is by the reconstitution of the contents of the second container with the contents of the first container and administration by a delivery device such as a syringe. The kit may also contain written matter such as a leaflet that indicates the use of the contents of the kit as a composition for vaccinating a subject to stimulate an immune response.

Qualitative and quantitative measurement of the immune response of a compound or composition can be implemented using methods known in the art, such as measuring antigen specific antibody production, activation of specific populations of lymphocytes such as CD4+ T cells or NK cells, and/or production of cytokines such as IFN, IL-2, IL-4 or IL-12. Methods for measuring specific antibody responses include enzyme-linked immunosorbent assay (ELISA) as known in the art. Measurement of numbers of specific types of lymphocytes such as CD4+ T cells can be achieved, for example, with fluorescence-activated cell sorting (FACS). Cytotoxicity assays can be performed, e.g., as described in Raz et al., (1994) Proc. Natl. Acad. Sci. USA 91:9519-9523. Serum concentrations of cytokines can be measured, for example, by ELISA. Such assays are described, e.g., in Selected Methods in Cellular Immunology (1980) Mishell and Shiigi, eds., W.H. Freeman and Co.

In one embodiment, a compound or composition, such as a tryptanthrin compound, is considered effective to elicit an immune response if a concentration of 20 µM (or alternatively 100 µM, or 200 µM, or 300 µM) of the tryptanthrin compound causes the production of TNF-a in an in vitro cell based assay of human peripheral blood mononuclear cells, wherein the concentration of the human peripheral blood mononuclear cells is about 500,000/mL, and wherein the cells are exposed to the compound for about 18-24 hours, e.g., about 24 hours.

An embodiment of the invention provides for a method of immunotherapy for the treatment of cancer comprising administering to a subject an immunostimulatory effective amount of a tryptanthrin derivative In another embodiment, a tryptanthrin compound or composition comprising a tryptanthrin compound is considered effective to reduce tumor growth or treat cancer when administered in an amount effective to illicit an immune response but in an amount insufficient to be directly cytotoxic to the tumor or cancer.

The above method of stimulating a local immune response for example in selected cells or tissues of a patient includes the stimulation of a local immune response wherein the selected cells or tissues are infected or cancerous. In one embodiment the selected cells or tissues are infected with a virus, parasite, fungus or bacterium.

The methods, compositions, and kits of the invention may be used wherein the antigen, as required, is derived from a bacterial, parasitic, viral, or fungal pathogen. When a bacterial pathogen is treated, the bacterial pathogen may be selected from the group consisting of diphtheria, *staphylococcus*, cholera, tuberculosis, tetanus, *streptococcus pneumoniae, streptoccus agalacitiae, streptococcus pyogenes, pertussis, Neisseria meningitis, Neisseria gonorrheae, chlamydia, Helicobacter pylori*, and *Hemophilius influenza* type B. When a viral pathogen is treated, the viral pathogen may be selected from the group consisting of viral meningitis, rhinovirus, influenza, respiratory syncytial virus, parainfluenza virus, rotavirus, tick borne encephalitis virus, coronaviridae, rhabodoviridiae, VZV, EBV, CMV, HIV, HPV, HSV, HAV, HBV, HCV, and SARS. When a parasitic pathogen is treated, the parasitic pathogen may be selected from the group consisting of *Plasmodium falciparum, Plasmodium ovale, Plasmodium malariae*, and *P. vivax*. The antigen may additionally associated with a disease selected from the group consisting of BCG, cholera, plague, typhoid, hepatitis B infection, influenza, inactivated polio, rabies, measles, mumps, rubella, oral polio, yellow fever, tetanus, diphtheria, *hemophilus influenzae* b, meningococcus infection, tick borne encephalitis, SARS, HCV, HIV, and pneumococcus infection. The methods, compositions, and kits of the invention stimulate an immune response wherein the immune response may be the cellular production of one or more cytokines.

The vaccine adjuvant compositions of the invention can contain further pharmaceutically acceptable ingredients, excipients, carriers, and the like well known to those skilled in the art.

In another embodiment methods of treating allergies are provided comprising administering a tryptanthrin compound alone or in combination with at one other agent known to be effective against allergies, wherein said combination is more effective in treating an allergic condition than the know agent(s) are without the addition of said tryptanthrin compound. In a more preferred embodiment the known agent is antihistamine and/or leukotriene inhibitor. In another preferred embodiment, the allergic condition is asthma. In another preferred embodiment, the allergic condition is selected from the group consisting of allergic rhinitis, dermatosis, and urticaria. In an even more preferred embodiment the combination is administered to a subject enterally, parenterally, intranasally, subcutaneously, or intraarterially.

The vaccine composition may include an additional non-tryptanthrin adjuvant. Preferred adjuvants to enhance effectiveness of the composition include, but are not limited to: (1) aluminium salts (alum), such as aluminum hydroxide, aluminum phosphate, aluminum sulfate, etc; (2) oil-in-water emulsion formulations (with or without specific immunostimulating agents such as muramyl peptides or bacterial cell wall components), such as, for example (a) MF59™ (WO90/14837), containing 5% squalene, 0.5% Tween 80, and 0.5% Span 85 (optionally containing MTP-PE) formulated into submicron particles using a microfluidizer, (b) SAF, containing 5% squalene, 0.5% Tween 80, 5% pluronic-blocked polymer L121, and thr-MDP either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as QS21 or Stimulon™ (Cambridge Bioscience, Worcester, Mass.) may be used or particles generated therefrom such as ISCOMs (immunostimulating complexes), which ISCOMs may be devoid of additional detergent e.g. WO00/07621; (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (6) momophosphoryl lipid A (MPL) or 3-O-deacylated MPL (3dMPL), optionally in the substantial absence of alum when used with pneumococcal saccharides e.g. WO00/56358; (7) combinations of 3dMPL with, for example, QS21 and/or oil-in-water emulsions e.g. EP-A-0835318; (8) oligonucleotides comprising CpG motifs, i.e. containing at least one CG dinucleotide, with 5-methylcytosine optionally being used in place of cytosine; (9) a polyoxyethylene ether or a polyoxyethylene ester e.g. WO99/52549; (10) a polyoxyethylene sorbitan ester surfactant in combination with an octoxynol (WO0121207) or a polyoxyethylene alkyl ether or ester surfactant in combination with at least one additional non-ionic surfactant such as an octoxynol (WO01/21152); (11) a saponin and an immunostimulatory oligonucleotide (e.g. a CpG oligonucleotide) (WO00/62800); (12) an immunostimulant and a particle of metal salt e.g WO00/23105; (13) a saponin and an oil-in-water emulsion e.g. WO99/11241; (14) a saponin (e.g. QS21)+3dMPL+IL-12 (optionally +a sterol) e.g. WO98/57659; (14) other substances that act as immunostimulating agents to enhance the effectiveness of the composition. In one particular embodiment, Alum (especially aluminium phosphate and/or hydroxide) and MF59 are preferred for use with saccharide antigens.

The invention is also directed to administering the vaccine adjuvant composition. The vaccine is administered in an amount effective to stimulate an immune response. The amount that constitutes an effective amount depends, inter alia, on the particular vaccine used, the particular adjuvant compound being administered and the amount thereof, the immune response that is to be enhanced (humoral or cell mediated), the state of the immune system (e.g., suppressed, compromised, stimulated), and the desired therapeutic result. Accordingly it is not practical to set forth generally the amount that constitutes an effective amount of the vaccine. Those of ordinary skill in the art, however, can readily determine the appropriate amount with due consideration of such factors.

Suitable vaccines include, but are not limited to, any material that raises either humoral or cell mediated immune response, or both. Suitable vaccines include live viral and bacterial immunogens and inactivated viral, tumor-derived, protozoal, organism-derived, fungal, and bacterial immunogens, toxoids, toxins, polysaccharides, proteins, glycoproteins, peptides, and the like. Conventional vaccines, such as those used in connection with BCG (live bacteria), cholera, plague, and typhoid (killed bacteria), hepatitis B, influenza, inactivated polio, and rabies (inactivated virus), measles, mumps, rubella, oral polio, and yellow fever (live virus), tetanus and diphtheria (toxoids), *hemophilus influenzae* b, meningococcal, and pneumococcal (bacterial polysaccharides) also can be used. Furthermore, it is contemplated that certain currently experimental vaccines, especially materials such as recombinant proteins, glycoproteins, and peptides that do not raise a strong immune response, will also find use in connection with the tryptanthrin adjuvant. Exemplary experimental subunit immunogens include those related to viral disease such as adenovirus, HIV, chicken pox, cytomegalovirus, dengue, feline leukemia, fowl plague, hepatitis A, hepatitis B, hepatitis C, HSV-1, HSV-2, hog cholera, influenza A, influenza B, Japanese encephalitis, measles, parainfluenza, rabies, respiratory syncytial virus, rotavirus, wart, and yellow fever.

Specific antigens for use with the invention include, but are not limited to, those listed below.

The invention may also comprise one or more bacterial, viral, or parasitic antigen. Antigens may be used alone or in any combination. (See, e.g., WO 02/00249 describing the use of combinations of bacterial antigens). The combinations may include multiple antigens from the same pathogen, multiple antigens from different pathogens or multiple antigens from the same and from different pathogens. Thus, bacterial, viral, and/or other antigens may be included in the same composition or may be administered to the same subject separately. It is generally preferred that combinations of antigens be used to raise an immune response be administered together.

Non-limiting examples of bacterial pathogens that may be used in the invention include chlamydia, diphtheria (See, e.g., Chapter 3 of *Vaccines*, 1998, eds. Plotkin & Mortimer (ISBN 0-7216-1946-0), staphylococcus (e.g., *Staphylococcus aureus* as described in Kuroda et al. (2001) *Lancet* 357:1225-1240), cholera, tuberculosis, *C. tetani*, also known as tetanus (See, e.g., Chapter 4 of *Vaccines*, 1998, eds. Plotkin & Mortimer (ISBN 0-7216-1946-0), *Streptococcus pneumoniae, Streptococcus agalactiae* and *Streptococcus pyogenes* as described, for example, in Watson et al. (2000) *Pediatr. Infect. Dis. J.* 19:331-332; Rubin et al. (2000) *Pediatr Clin. North Am.* 47:269-284; Jedrzejas et al. (2001) *Microbiol Mol Biol Rev* 65:187-207; Schuchat (1999) *Lancet* 353:51-56; GB patent applications 0026333.5; 0028727.6; 015640.7; Dale et al. (1999) *Infect Dis Clin North Am* 13:227-1243; Ferretti et al. (2001) *PNAS USA* 98:4658-4663), pertussis (See, e.g., Gusttafsson et al. (1996) *N. Engl. J. Med.* 334:349-355; Rappuoli et al. (1991) *TIBTECH* 9:232-238), meningitis, *Moraxella catarrhalis* (See, e.g., McMichael (2000) *Vaccine* 19 Suppl. 1:S101-107) and other pathogenic states, including, without limitation, *Neisseria meningitides* (A, B, C, Y), *Neisseria gonorrhoeae* (See, e.g., WO 99/24578; WO 99/36544; and WO 99/57280), *Helicobacter pylori* (e.g., CagA, VacA, NAP, HopX, HopY and/or urease as described, for example, WO 93/18150; WO 99/53310; WO 98/04702) and *Haemophilus influenza*. *Hemophilus influenza* type B (HIB) (See, e.g., Costantino et al. (1999) *Vaccine* 17:1251-

1263), *Porphyromonas gingivalis* (Ross et al. (2001) *Vaccine* 19:4135-4132) and combinations thereof.

Non-limiting examples of viral pathogens that may be used in the invention include viral meningitis, rhinovirus, influenza (Kawaoka et al., *Virology* (1990) 179:759-767; Webster et al., "Antigenic variation among type A influenza viruses," p. 127-168. In: P. Palese and D. W. Kingsbury (ed.), Genetics of influenza viruses. Springer-Verlag, New York), respiratory syncytial virus (RSV), parainfluenza virus (PIV), rotavirus (e.g., VP1, VP2, VP3, VP4, VP6, VP7, NSP1, NSP2, NSP3, NSP4 or NSP5 and other rotavirus antigens, for example as described in WO 00/26380) and the like. Antigens derived from other viruses will also find use in the present invention, such as without limitation, proteins from members of the families Picornaviridae (e.g., polioviruses, etc. as described, for example, in Sutter et al. (2000) *Pediatr Clin North Am* 47:287-308; Zimmerman & Spann (1999) *Am Fam Physician* 59:113-118; 125-126); Caliciviridae; Togaviridae (e.g., rubella virus, etc.); Flaviviridae, including the genera flavivirus (e.g., yellow fever virus, Japanese encephalitis virus, serotypes of Dengue virus, tick borne encephalitis virus, West Nile virus, St. Louis encephalitis virus); pestivirus (e.g., classical porcine fever virus, bovine viral diarrhea virus, border disease virus); and hepacivirus (e.g., hepatitis A, B and C as described, for example, in U.S. Pat. Nos. 4,702,909; 5,011,915; 5,698,390; 6,027,729; and 6,297,048); Parvovirus (e.g., parvovirus B19); Coronaviridae; Reoviridae; Bimaviridae; Rhabodoviridae (e.g., rabies virus, etc. as described for example in Dressen et al. (1997) *Vaccine* 15 Suppl:s2-6; MMWR Morb Mortal Wkly Rep. 1998 January 16:47(1):12, 19); Filoviridae; Paramyxoviridae (e.g., mumps virus, measles virus, respiratory syncytial virus, etc. as described in Chapters 9 to 11 of *Vaccines*, 1998, eds. Plotkin & Mortimer (ISBN 0-7216-1946-0); Orthomyxoviridae (e.g., influenza virus types A, B and C, etc. as described in Chapter 19 of *Vaccines*, 1998, eds. Plotkin & Mortimer (ISBN 0-7216-1946-0); Bunyaviridae; Arenaviridae; Retroviradae (e.g., HTLV-1; HTLV-11; HIV-1 (also known as HTLV-III, LAV, ARV, HTI, R, etc.)), including but not limited to antigens from the isolates HIVIIIb, HIVSF2, HIVLAV, HIVI-AL, I-IIVMN, SF162); HIV-I CM235, HIV-I US4; HIV-2; simian immunodeficiency virus (SIV) among others. Additionally, antigens may also be derived from human papilloma virus (HPV) and the tick-borne encephalitis viruses. See, e.g. Virology, $3^{rd}$ Edition (W. K. Joklik ed. 1988); Fundamental Virology, $2^{nd}$ Edition (B. N. Fields and D. M. Knipe, eds, 1991), for a description of these and other viruses.

Proteins may also be derived from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH (See, U.S. Pat. No. 4,689,225 and PCT Publication WO 89/07143); and antigens derived from other human herpesviruses such as HHV6 and HHV7. (See, e.g. Chee et al., *Cytomegaloviruses* (J. K. McDougall, ed., Springer-Verlag 1990) pp. 125-169, for a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J. Gen. Virol.* (1986) 67:1759-1816, for a review of VZV). Herpes simplex virus (HSV) rgD2 is a recombinant protein produced in genetically engineered Chinese hamster ovary cells. This protein has the normal anchor region truncated, resulting in a glycosylated protein secreted into tissue culture medium. The gD2 can be purified in the CHO medium to greater than 90% purity. Human immunodeficiency virus (HIV) env-2-3 is a recombinant form of the HIV enveloped protein produced in genetically engineered *Saccharomyces cerevisae*. This protein represents the entire protein region of HIV gp120 but is non-glycosylated and denatured as purified from the yeast. HIV gp120 is a fully glycosylated, secreted form of gp120 produced in CHO cells in a fashion similar to the gD2 above. Additional HSV antigens suitable for use in immunogenic compositions are described in PCT Publications WO 85/04587 and WO 88/02634, the disclosures of which are incorporated herein by reference in their entirety. Mixtures of gB and gD antigens, which are truncated surface antigens lacking the anchor regions, are particularly preferred.

Antigens from the hepatitis family of viruses, including hepatitis A virus (HAV) (See, e.g., Bell et al. (2000) *Pediatr Infect Dis. J.* 19:1187-1188; Iwarson (1995) *APMIS* 103:321-326), hepatitis B virus (HBV) (See, e.g., Gerlich et al. (1990) *Vaccine* 8 Suppl:S63-68 & 79-80), hepatitis C virus (HCV) (See, e.g., PCT/US88/04125, published European application number 318216), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. Also included in the invention are molecular variants of such polypeptides, for example as described in PCT/US99/31245; PCT/US99/31273 and PCT/US99/31272. The HCV genome encodes several viral proteins, including E1 (also known as E) and E2 (also known as E2/NSI) and an N-terminal nucleocapsid protein (termed "core") (see, Houghton et al., *Hepatology* (1991) 14:381-388, for a discussion of HCV proteins, including E1 and E2). Similarly, the sequence for the d-antigen from HDV is known (see, e.g., U.S. Pat. No. 5,378,814) and this antigen can also be conveniently used in the present composition and methods. Additionally, antigens derived from HBV, such as the core antigen, the surface antigen, SAg, as well as the presurface sequences, pre-S1 and pre-S2 (formerly called pre-S), as well as combinations of the above, such as SAg/pre-S1, SAg/pre-S2, SAg/pre-S1/pre-S2, and pre-S1/pre-S2, will find use herein. See, e.g., "HBV Vaccines—from the laboratory to license: a case study" in Mackett, M. and Williamson, J. D., *Human Vaccines and Vaccination*, pp. 159-176, for a discussion of HBV structure; and U.S. Pat. Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464. Each of these proteins, as well as antigenic fragments thereof, will find use in the present composition and methods.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al., "Antigenic variation among type A influenza viruses," p. 127-168. In: P. Palese and D. W. Kingsbury (ed.), *Genetics of influenza viruses*. Springer-Verlag, New York). Thus, proteins derived from any of these isolates can also be used in the compositions and methods described herein.

Non-limiting examples of parasitic antigens include those derived from organisms causing malaria and Lyme disease.

Specific antigens include: a protein antigen from *N. meningitides* serogroup B (WO99/24578, WO99/36544, WO99/57280, WO00/22430, WO96/29412, Tettelin et al. (2000) Science 287:1809-1815, Pizza et al. (2000) Science 287:1816-1820); an outer-membrane vesicle (OMV) preparation from *N. meningitides* serogroup B. (WO01/52885, Bjune et al. (1991) Lancet 338(8775), Fuskasawa et al. (1999) Vaccine 17:2951-2958, Rosenqist et al. (1998) Dev. Biol. Strand 92:323-333); a saccharide antigen from *N. meningitides* serogroup A, C W135 and/or Y, such as the oligosaccharide (Constantino et al. (1992) Vaccine 10:691-698) from serogroup C (Constantino et al. (1999) Vaccine 17:1251-1263); a saccharide antigen from *Streptocaccus pneumoniae* (Watson (2000) Pediatr Infect Dis J 19:331-332, Rubin (2000) Pediatr Clin North Am 47:269-285, Jedrzejas (2001) Microbiol Mol Biol Rev 65:187-207); an antigen from *N. gonorrhoeae* (WO99/24578, WO99/36544, WO99/57280); an antigen from *Chlamydia pneumoniae* (Kalman et al. (1999) Nature Genetics 21:385-389, Read et al. (2000) Nucleic Acids Res 28:1397-406, Shirai et al. (2000) J. Infect. Dis 181(Suppl 3):S524-S527, WO99/27105, WO00/27994, WO00/37494); an antigen from *Chlamydia trachomatis* (WO99/28475); an antigen from hepatitis A virus, such as inactived virus (Bell (2000) Pediatr Infect Dis J 19:1187-1188, Iwarson (1995) APMIS 103:321-326); an antigen from hepatitis B virus, such as the surface and/or core antigens (e.g. Iwarson (1995) APMIS 103:321-326, Gerlich et al. (1990) Vaccine 8 Suppl: S63-68 & 79-80); an antigen from hepatitis C virus (Hsu et al. (1999) Clin Liver Dis 3:901-915); an antigen from *Bordetella pertussis*, such as petussis holotoxin (PT) and filamentous haemagglutinin (FHA) from *B. pertussis*, optionally also combination with pertactin and/or agglutinogens 2 and 3 (Gastofsson et al. (1996) N. Engl. J. Med. 334-349-355, Rappuoli et al. (1991) TIBTECH 9:232-238); a diphtheria antigen, such as a diphtheria toxoid (Vaccines (1988) eds. Plotkin & Mortimer. ISBN 0-7216-1946-0:chapter 3) e.g. the $CRM_{197}$ mutant (Del Guidice et al. (1998) Molecular Aspects of Medicine 19:1-70); a tetanus antigen, such as a tetanus toxoid (Vaccines (1988) eds. Plotkin & Mortimer. ISBN 0-7216-1946-0:chapter 4); a protein antigen from *Helicobacter pylori* such as CagA (WO93/018150), VacA (WO93/018150), NAP (WO99/53310), HopX (Tettelin et al. (2000) Science 287:1809-1815), HopY (WO98/04702) and/or urease; a saccharide antigen from *Haemophilus influenzae* B (Constantino et al. (1999) Vaccine 17:1251-1263); an antigen from *Porphyromonas gingivalis* (Ross et al. (2001) Vaccine 19:135-142); polio antigen(s) (Sutter et al. (2000) Pediatr Clin North Am 47:287-308, Zimmerman & Spann (1999) Am Fan Physician 59:113-118, 125-126) such as IPV or OPV; rabies antigen(s) (Dreensen (1997) Vaccine 15 Suppl"S2-6) such lyophilized inactivated virus (MMWR Morb Mortal Wkly rep 1998 January 16:47(1):12, 9, RabAvert™); measles, mumps and/or rubella antigens (Vaccines (1988) eds. Plotkin & Mortimer. ISBN 0-7216-1946-0: chapters 9, 10, & 11); influenza antigen(s) (Vaccines (1988) eds. Plotkin & Mortimer. ISBN 0-7216-1946-0:chapter 19), such as the haemagglutinin and/or neuraminidase surface proteins; an antigen from *Moraxella catarrhalis* (McMichael (2000) Vaccine 19 Suppl 1:S101-107); an antigen from *Streptococcus agalactiae* (group B *streptococcus*) (Schuchat (1999) Lancer 353(9146):51-6, GB patent applications 0026333.5, 0028727.6 & 0105640.7); an antigen from *Streptococcus pyogenes* (group A *streptococcus*) (GB patent applications 0026333.5, 0028727.6 & 0105640.7, Dale (1999) Infect Disclin North Am 13:227-43, Ferretti et al. (2001) PNAS USA 98: 4658-4663); and an antigen from *Staphylococcus aureus* (Kuroda et al. (2001) Lancet 357(9264):1225-1240; see also pages 1218-1219).

The composition may comprise one or more antigens.

Where a saccharide or carbohydrate antigen is used, it is preferably conjugated to a carrier protein in order to enhance immunogenicity (Ramsay et al. (2001) Lancet 357(9251): 195-196, Lindberg (1999) Vaccine 17 Suppl 2:S28-36, Buttery & Moxon (2000) J R Coil Physicians Long 34:163-168, Ahmad & Chapnick (1999) Infect Dis Clin North Am 13:113-133, vii, Goldblatt (1998) J. Med. Microbiol. 47:663-567, European Patent 0 477 508, U.S. Pat. No. 5,306,492, WO98/42721, Conjugate Vaccines (eds. Cruse et al.) ISBN 3805549326, particularly vol. 10:48-114, Hermanson (1996) Bioconjugate Techniques ISBN: 012323368 & 012342335X). Preferred carrier proteins are bacterial toxine or toxiods, such as diphtheria or tetanus toxids. The $CRM_{197}$ diphtheria toxoid is particularly preferred. Other suitable carrier proteins include the *N. meningitides* outer membrane protein (European Patent Application 0372501), synthetic peptides (European Patent Application 0378881, European Patent Application 0427347), heat shock proteins (WO93/17712), pertussis proteins (WO98/58668, European Patent Application 0471177), protein D from *H. influenzae* (WO00/56360), toxin A or B from *C. difficile* (WO00/67161) etc. Where a mixture comprises capsular saccharides from both serogroups A and C, it is preferred that the ratio (w/w) of MenA saccharide:MenC saccharide is greater than 1 (e.g. 2:1, 3:1, 4:4, 5:1, 10:1 or higher). Saccharides from different serogroups of *N. meningitides* may be conjugated to the same or different carrier proteins.

Any suitable conjugation reaction can be used, with any suitable linker where necessary. Toxic protein antigens may be detoxified where necessary (e.g. detoxification of pertussis toxin by chemical and/or genetic means (30)). Where a diphtheria antigen is included in the composition it is preferred also to include tetanus antigens and pertussis antigens. Similar, where a tetanus antigen is include it is preferred also to include diphtheria and pertussis antigens. Similar, where pertussis antigen is included it is preferred also to include diphtheria and tetanus antigens.

In another embodiment, the invention provides a method of modulating tumor growth in a mammal comprising administering to the mammal any tryptanthrin compound described herein, wherein the tryptanthrin compound is a tryptanthrin derivative. The term "tryptanthrin derivative" thus refers to a modified form of tryptanthrin, many examples of which are described herein, but does not include the naturally produced tryptanthrin molecule (indolo-[2,1-b]quinazolin-6,12-dione) itself.

The pharmaceutical compositions containing the tryptanthrin compounds described herein can include additives such as excipients. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Other additives include immunostimulatory agents known in the art. Immunostimulatory oligonucleotides and polynucleotides are described in PCT WO 98/55495 and PCT WO 98/16247. U.S. Patent Application No. 2002/0164341 describes adjuvants including an unmethylated CpG dinucleotide (CpG ODN) and a non-nucleic acid adjuvant. U.S. Patent Application No. 2002/0197269 describes compositions comprising an antigen, an immunogenic CpG-ODN and a polycationic polymer. Other immunostimulatory additives described in the art may be used, for example, as described in U.S. Pat. No. 5,026,546; U.S. Pat. No. 4,806,352; and U.S. Pat. No. 5,026,543.

A controlled release delivery system may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation spray, rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intramuscular, intraperitoneal, intranasal, subdural, rectal, and the like. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

Effective amounts of the compounds of the invention generally include any amount sufficient to detectably treat viral infections.

Successful treatment of a subject in accordance with the invention may result in the inducement of a reduction or alleviation of symptoms in a subject afflicted with a medical or biological disorder to, for example, halt the further progression of the disorder, or the prevention of the disorder.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

While the compounds of the invention can be administered as the sole active pharmaceutical agent, they can also be used in combination with one or more other agents used in the treatment of disorders. Representative agents useful in combination with the compounds of the invention for the treatment of viral infections include, for example, Interferon, Ribavirin, and the like.

When additional active agents are used in combination with the compounds of the present invention, the additional active agents may generally be employed in therapeutic amounts as indicated in the PHYSICIANS' DESK REFERENCE (PDR) 53$^{rd}$ Edition (1999), which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

Compounds of the present invention can be readily synthesized using the methods described herein, or other methods, which are well known in the art.

In general, the compounds of the invention can be prepared by the processes illustrated in Schemes I (FIG. 1), II (FIG. 2), and III (FIG. 3), as described in U.S. Pat. No. 5,441,955. According to the reaction Scheme I substituted isatin derivatives 3 are prepared by four methods. The first method involves reaction of substituted anilines with hydroxylamine and chloral hydrate in aqueous hydrochloric acid according to the procedure of T. Sandmeyer et al., *Helv. Chim. Acta.* 2:234 (1919) and C. S. Marvel et al., *Org. Syn. Coll.* 1:327 (1941) to give the anilides 2. Cyclization of anilides 2 to isatins 3 is effected by treating compound 2 in hot concentrated sulfuric acid. A second synthesis of isatins 3 from anilines 1 was accomplished using the procedures of Gassman et al. *J. Org. Chem.*, 42:1344 (1977). Thus, reaction of aniline 1 with t-butylhypochlorite at −70° C. followed by ethyl thiomethylacetate, triethylamine and warming the reaction mixture to room temperature gave the anilino esters 4. Esters 4 were not isolated but were cyclized to the oxindoles 5 using aqueous hydrochloric acid. Oxindoles 5 were converted to isatins 3 by oxidation with N-chlorosuccinimide and mercuric oxide. A third method for the synthesis of isatins 3 involves the metalation of t-butyloxycarbonylanilines 6 with alkyllithium reagents (for example, n-butyllithium, sec-butyllithium, tert-butyllithium) in an inert and dry solvent such as tetrahydrofuran (THF), dimethoxyethane (DME), dioxane and the like. The resultant dianion is reacted with esters or amides of oxalic acid (for example, diethyl oxalate, ethyl oxalochloride, N-methyl, N-methoxy oxalamide, the half ester/amide, ethyl N-methyl, N-methoxy oxalamide) in the presence of a Lewis acid such as magnesium bromide, boron trifluoride, copper (I) iodide and the like to give the alpha ketoester 7. Deprotection of the Boc group and cyclization to isatins 3 is accomplished using HCl or trifluoroacetic acid in methanol, dichloromethane, dioxane, diethyl ether and the like. A fourth and final method for the preparation of isatins 3 involves the reaction of N-allyl isatoic anhydrides 10b with potassium cyanide according to the procedure of G. Coppola *J. Heterocyclic Chem.* 7:827 and 1501 (1979). The resulting N-allylisatins are reacted with palladium (0) then aqueous acid to give isatins 3. The required N-allyl isatoic anhydrides are prepared by reaction of isatoic anhydrides 10a with strong bases (for example, sodium hydride, potassium hydride or t-butoxide, lithium diisopropylamide and the like) in an inert solvent such as tetrahydrofuran, dimethylformamide, N-methylpyrrolidinone with allyl bromide at low temperature (for example, −50° C. to ambient temperature). Isatoic anhydrides are prepared from either 2-aminocarboxylic acid derivatives 8 or isatins 3 (see G. Coppola, *Synthesis* 505-536, 1980, and references cited therein).

Figure 2:
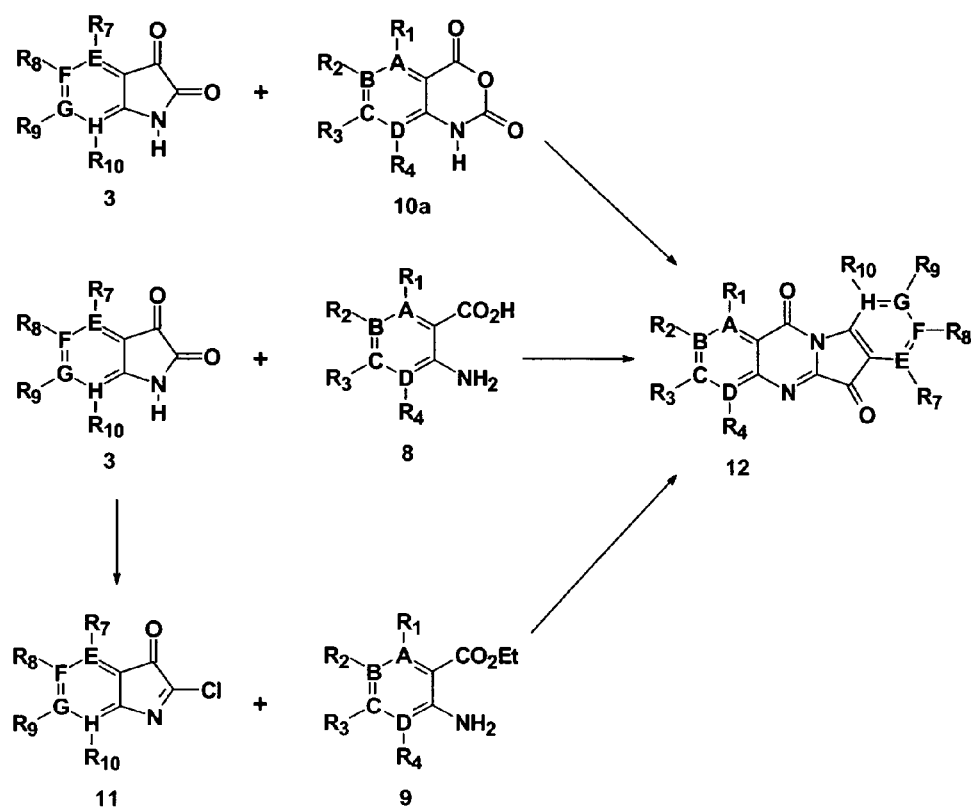
FIG. 2 is a schematic representation of alternative synthesis pathways of the indolo[2,1-b]quinazoline-6,12-dione compounds.

Referring now to FIG. 2, Scheme II illustrates the preparation of indolo[2,1-b]quinazoline derivatives from substituted isatin 3. Reaction of isatin 3 with a strong base such as sodium hydride, potassium hydride or t-butoxide, 1,8-diaza[5,4,1]bicycloundec-7-ene (DBU) and the like in an inert solvent (for example, tetrahydrofuran, dimethylformamide, N-methylpyrrolidinone or pyridine) and isatoic anhydride 10a in dimethylaminopyridine (DMAP) gives the indolo[2,1-b]quinazoline derivatives 12. A second synthesis of the indoloquinazolines 12 was accomplished by reaction of isatins 3 with 2-aminobenzoic acids or 2-aminopyrididine carboxylic acids with a peptide coupling reagent, such as hydroxybenzotriazole (HOBT)/dicyclohexylcarbodiimide (DCC) or 2-[1H-benzotriazole-1-yl]-1,1,3,3,-tetramethyluronium hexaflurorphosphate (HBTU) and the like. The peptide coupling reaction may be conducted in a polar aprotic solvent (for example, dimethylformamide (DMF), N-methylpyrrolidone (NMP), tetrahydrofuran (THF) with a base such as 1,8-diaza[5,4,1]bicycloundec-7-ene (DBU), pyridine, N-methylmorpholine and the like. A third synthesis of compounds 12 may be obtained by the reaction of isatins 3 with iminoyl chlorides 11. Reaction of isatins 3 with chlorinating reagent (for example, phosphorus pentachloride, phosphorus oxychloride, thionyl chloride, oxalyl chloride and the like) give the isatin iminoyl chloride 11. Reaction of the iminoyl chloride 11 with the amino ester 9 in acetic acid, dichloroethane or tetrahydrofuran gives the indolo[2,1-b] quinazoline.

Figure 3:
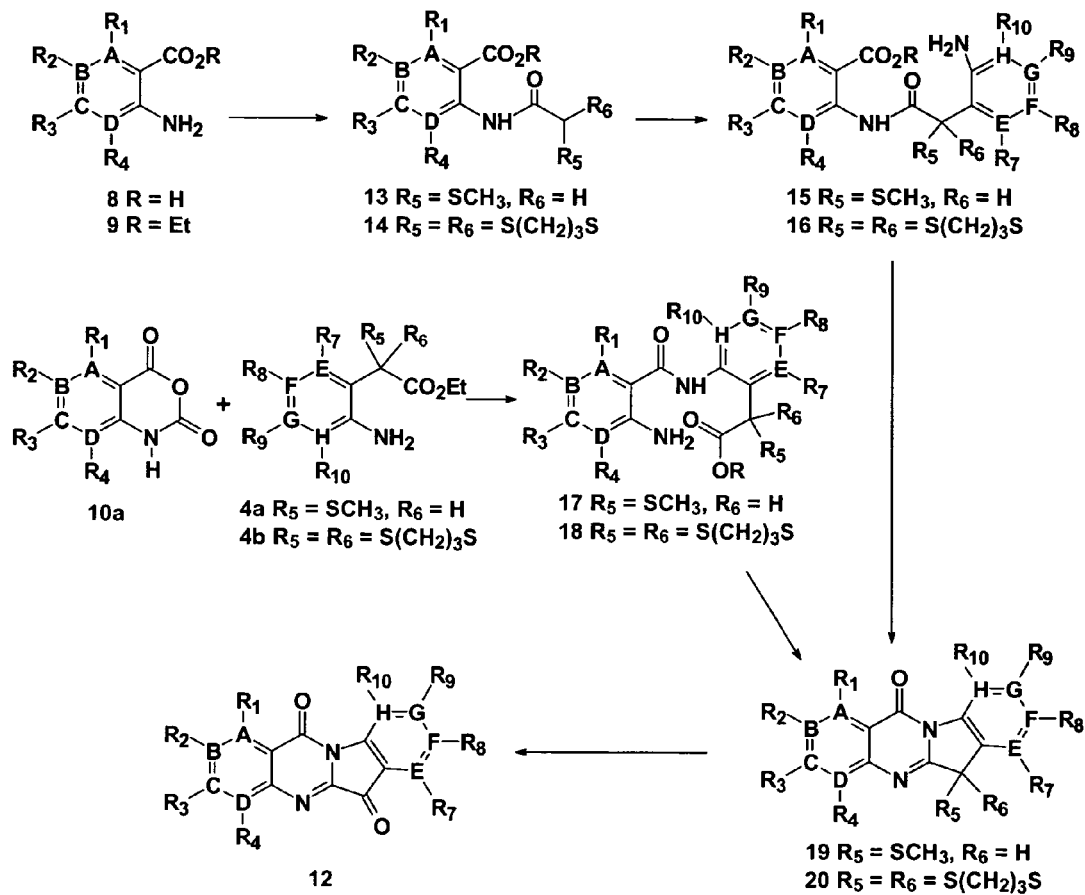
FIG. 3 is a schematic representation of an alternative synthesis pathway of tryptanthrin compounds.

Referring now to FIG. 3, Scheme III illustrates two alternative methods for the preparation of indolo[2,1-b]quinazolines 12. The first method involves the reaction of ester 9 or acid 8 with either methylthioacetic acid or 1,3-dithiane-2-carboxylic acid and a coupling reagent (for example, DCC/HOBT/DMAP, carbonyldiimidazole (CDI) and the like) to give the amides 13 and 14, respectively (R=H or ethyl). Amides 13 and 14 are reacted with aniline 1 using the procedure described previously to afford compounds 15 and 16. In the case where R=ethyl, the ester is hydrolyzed using an alkaline bases such as sodium hydroxide, lithium hydroxide in water, aqueous ethanol, dioxane or tetrahydrofuran and the like. The resulting amino acids 15 and 16 are cyclized to give the indolo[2,1-b]quinazoline skeleton 19 and 20 using the procedure described by A. Singh et al. *Ind. J. Chem.* 7:881-883 (1969) (dicyclocarbodiimide (DCC) in benzene for 4-10 h at reflux temperature). The indolo[2,1-b]quinazoline derivatives 12 are obtained from 19 by oxidation with NCS/mercuric oxide and from 20 by dithiane hydrolysis (for example, the dithiane group is hydrolyzed using N-bromosuccinimide (NBS) in aqueous acetone (see E. Cain et al. *Tetrahedron Lett.* 1353 (1975)). Alternatively, amino ester 4a or 4b ($R_5$=H, $R_6$=$SCH_3$ or $R_5$=$R_6$=$S(CH_2)_3S$, prepared from aniline 1 and ethyl methylthioacetate and ethyl 1,3-dithiane-2-carboxylate, respectively) reacts with anhydride 10a using DMAP as a catalyst in an inert solvent (for example, tetrahydrofuran, dimethylformamide, N-methylpyrrolidinone and pyridine) to give the amides 17 and 18. The amino esters 17 and 18 are hydrolyzed as previously described to give the amino acids which are cyclized to indolo[2,1-b]quinazolines 19 and 20.

The compounds can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The foregoing may be better understood by reference to the following examples, which are presented for illustration and not to limit the scope of the inventive concepts.

All patents, patent applications and publications referred to herein are hereby incorporated herein by reference in their entirety.

EXAMPLES

Synthesis 1 as Described in U.S. Pat. No. 5,441,955.
Preparation of 5,6-difluoroisatin and 4,5-difluoroisatin

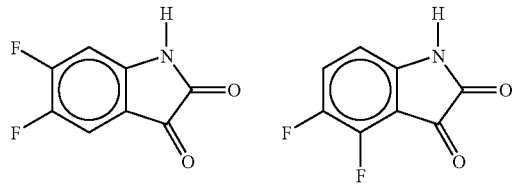

To a solution of 3,4-difluoroaniline (12.98 g, 0.100 mol) in 325 mL of methylene chloride at −65° C. was added a solution of t-butylhypochlorite (10.86 g, 0.100 mol) in 52 mL of methylene chloride. The mixture was stirred for 10 min. A solution of ethyl thiomethylacetate (13.49 g, 0.100 mol) in 65 mL of methylene chloride was added dropwise to the mixture and stirred at −65° C. for 1 h. Triethylamine (10.17 g, 0.100 mol) in 65 mL of methylene chloride was added and the reaction mixture was warmed to room temperature and stirred for 3 h. Water was added and the methylene chloride layer was separated and concentrated under reduced pressure to yield an oil. The resulting oil was diluted with 300 mL of diethyl ether and 80 mL of 2N HCl, and stirred for 24 h. A precipitate was formed, filtered and washed with 50 mL of diethyl ether to give a mixture of 5,6- and 4,5-difluoro-3-thiomethyloxindoles in 70% yield.

The crude oxindoles (11.64 g, 0.054 mol) were reacted with N-chlorosuccinimide (7.26 g, 0.05 mol) in 500 mL of chloroform at room temperature for 1 h. The reaction mixture was concentrated and the resulting residue was dissolved in 70 mL of THF. To this solution was added red mercury (II) oxide (11.78 g, 0.054 mol), boron trifluoride etherate (7.72 g, 0.05 mol), and 400 mL of aqueous 20% THF. The slurry was stirred for 3 h, diluted with 1000 mL of chloroform and filtered through celite. The resulting solids were washed with chloroform and the chloroform layer was separated and concentrated. Chromatography on silica gel eluting with 1% isopropyl alcohol:chloroform gave 5,6-difluoroisatin (Saul Kadin, U.S. Pat. No. 4,721,712) and 4,5-difluoroisatin in 31% and 4% yield, respectively. 4,5-Difluoroisatin: mp 140° C. (dec); $^1$H NMR (300 MHz, DMSO-d$_6$) δ 11.25 (s, 1H), 7.7 (dd, 1H), 6.7 (dd, 1H).

Synthesis 2 as described in U.S. Pat. No. 5,441,955.
5,6,7-Trifluoroisatin:

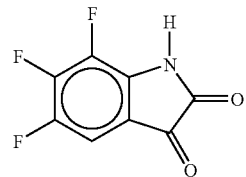

Using the procedure in Synthesis I and substituting 2,3,4-trifluoroaniline for 3,4-difluoroaniline gave 5,6,7-trifluoro-3-methylthiooxindole in 51% yield: mp 177-178.5° C.; $^1$H NMR (300 MHz, DMSO-d$_6$) δ 11.3 (s, 1H) 7.30-7.39 (m, 1H) 4.65 (s, 1H) 1.95 (s, 3H). 5,6,7-trifluoroisatin was obtained in an overall yield of 37.5%: mp 192.8-194.3° C.; $^1$H NMR (300 MHz, DMSO-d$_6$) δ 11.8 (s, 1H) 7.60-7.75 (m, 1H).

Synthesis 3 as Described in U.S. Pat. No. 5,441,955.
5,7-Difluoroisatin:

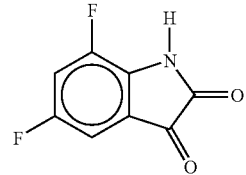

Using the procedure in Synthesis 1 and substituting 2,4-difluoroaniline for 3,4-difluoroaniline gave 5,7-difluoro-3-methylthiooxindole in 57% yield: mp 150.7-152.0° C.; $^1$H NMR (300 MHz, DMSO-d$_6$) δ 11.1 (s, 1H) 7.16-7.43 (m, 1H) 7.01-7.12 (m, 1H) 4.7 (s, 1H) 1.93 (s, 3H); MS (M+CH$_4$CN)$^+$ 257. 5,7-difluoroisatin was obtained in an overall yield of 39% yield: mp 188.5-194° C.; $^1$H NMR (300 MHz, DMSO-d$_6$) δ 11.6 (s, 1H) 7.60-7.73 (m, 1H) 7.43-7.4 (m, 1H).

Synthesis 4 as Described in U.S. Pat. No. 5,441,955.
5-Fluoro-6-(4-methylpiperazinyl)isatin:

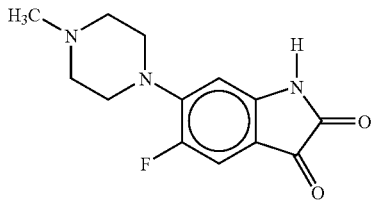

To a solution of 5,6-difluoroisatin (1.0 g, 5 mmol) in 50 mL of dimethyl sulfoxide was added N-methylpiperazine (5.47 g, 50 mmol). The mixture was stirred for 4 h at room temperature and the crude reaction mixture was diluted with ethyl acetate. The organic solution was washed with saturated sodium bicarbonate. The organic layers were separated and concentrated to give the title compound in 72% yield: mp 150° C. (dec); $^1$H NMR (300 MHz, DMSO-d$_6$) δ 10.8 (br s, 1H), 7.3 (d, 1H), 6.4 (d, 1H), 2.25 (s, 3H), 2.2 (m, 4H), 2.1 (m, 4H).

Synthesis 5 as Described in U.S. Pat. No. 5,441,955.
5-Fluoro-6-(3-methyl-4-tertbutyloxycarbonyl piperazinyl)isatin:

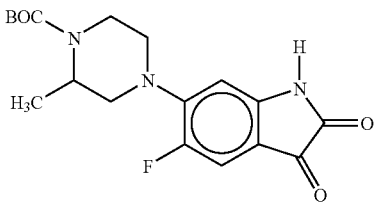

To a solution of 5-fluoro-6-(3-methylpiperazinyl)isatin (0.585 g, 2 mmol) in 30 mL of dry THF was added dropwise di-t-butyldicarbonate (0.727 g, 3 mmol) in 5 mL of THF. The mixture was stirred for 2 h at room temperature and the crude mixture was concentrated under reduced pressure. Chromatography of the residue on silica gel using methanol:chloroform as eluent gave the title compound in 69% yield: mp 160° C. (dec); $^1$H NMR (300 MHz, CDCl$_3$) δ 8.8 (br s, 1H), 7.3 (s, 1H), 6.4 (d, 1H), 4.35 (br s, 1H), 4.0 (d, 1H), 3.65 (t, 2H), 3.3 (dt, 1H), 3.25 (dt, 1H), 3.1 (t, 1H), 1.5 (s, 9H), 1.3 (s, 3H).

Synthesis 6 as Described in U.S. Pat. No. 5,441,955.
5,7-Difluoro-6-(4-methylpiperazinyl)isatin:

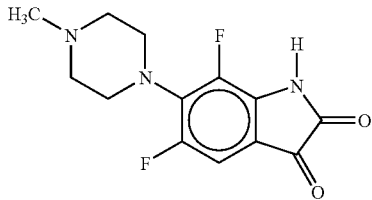

Using the procedure in Synthesis 4 and substituting 5,6,7-trifluoroisatin for 5,6-difluoroisatin gave the title compound in 70% yield.

Synthesis 7 as Described in U.S. Pat. No. 5,441,955.
5-Methoxyisatin

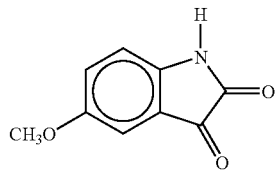

To a stirred solution of 12.6 g (75.6 mmol) of chloral hydrate in 168 mL water was added the following: 180 g (1.27 mole) sodium sulfate; 7.67 g (62.4 mmol) 4-methoxyaniline in 6 mL of concentrated HCl and 42 mL of water; and 15.4 g (224 mmol) of hydroxylamine hydrochloride in 70 mL of water. The mixture was heated slowly to 100° C. and kept at that temperature for 1 h. The mixture was cooled to room temperature, filtered and the precipitate washed with water and dried to give 81% yield of the anilide: $^1$H NMR (300 MHz, DMSO-d$_6$) δ 12.15 (s, 1H) 10.1 (s, 1H) 7.65 (s, 1H) 7.6 (d, 2H) 6.95 (d, 2H) 3.75 (s, 3H).

The crude anilide (10.8 g, 61 mmol) was added to 27 mL of concentrated sulfuric acid at 50° C., heated at 65° C. for 1 h, cooled to room temperature, and poured into 300 mL of ice. The solids were filtered and dried in vacuo over P$_2$O$_5$. The crude isatin was dissolved in boiling CH$_2$Cl$_2$ with 2% N-methylpyrrolidone and applied to a silica gel column. The product was eluted using a CH$_2$Cl$_2$:MeOH gradient 100% CH$_2$Cl$_2$ to (9:1) CH$_2$Cl$_2$:MeOH. 5-Methoxyisatin was obtained in 12% yield overall: mp 168-172° C.; $^1$H NMR (300 MHz, DMSO-d$_6$) δ 10.85 (s, 1H) 7.17-7.24 (m, 1H) 7.1 (d, 1H) 6.87 (d, 1H) 3.75 (s, 3H); MS (M+CH$_4$CN)$^+$ 158.

Synthesis 8 as Described in U.S. Pat. No. 5,441,955.
5-Azaisatin:

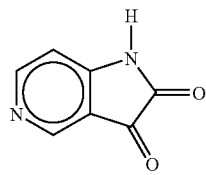

To a solution of 5-azaisatoic anhydride (1 mmol, Coppola, G. M. Synthesis 1980, 505) and allyl bromide (1.1 mmol) in DMF is added triethylamine (1.2 mmol) dropwise. The reaction mixture is allowed to stir at room temperature for 12 h after which time CHCl$_3$ is added and the organic layer is washed with water, dried (MgSO$_4$) and the solvent is evaporated to give N-allyl-5-azaisatoic anhydride.

A solution of N-allyl-5-azaisatoic anhydride (20 mmol) in DMF is added dropwise to a suspension of pulverized potassium cyanide (21 mmol) in DMF at 100° C. The reaction mixture is stirred at 100° C. for an additional 5 min after which time the mixture is poured into cold water and extracted with ether. The organic layer is dried (Na$_2$SO$_4$), filtered and the solvent is removed. Stirring the resulting residue in 2N hydrochloric acid overnight and adjusting the pH to 7 gives, upon filtration, N-allyl-5-azaisatin.

A solution of N-allyl-5-azaisatin (5.3 mmol), (Ph$_3$P)$_3$RhCl (0.5 mmol) in aqueous toluene is stirred under a nitrogen atmosphere at room temperature overnight. The organic layer is dried (MgSO$_4$) and the solvent is evaporated. The residue is stirred in 1N HCl/MeOH for 15 min after which time the methanol is evaporated and the pH of the water is adjusted to 7. A precipitate is formed and purified by silica gel chromatography (1% MeOH:CHCl$_3$) to obtain the title compound.

Synthesis 9 as Described in U.S. Pat. No. 5,441,955.
6-Azaisatin:

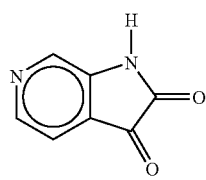

Using the procedure in Synthesis 8 and substituting 4-azaisatoic anhydride (Coppola, G. M. Synthesis 1980, 505) for 5-azaisatoic anhydride gives the title compound.

Synthesis 10 as Described in U.S. Pat. No. 5,441,955.
7-Azaisatin:

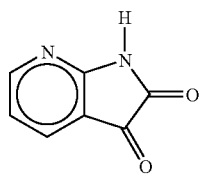

To a solution of 2-aminonicotinic acid (5 mmol) and sodium carbonate (5.1 mmol) in water is added triphosgene (1.6 mmol) at room temperature. The reaction mixture is allowed to stir for 16 h after which time the pH is adjusted to 3 and the resulting precipitate, 3-azaisatoic anhydride, is filtered.

Using the procedure in Synthesis 8 and substituting 3-azaisatoic anhydride for 5-azaisatoic anhydride, gives the title compound.

Synthesis 11 as Described in U.S. Pat. No. 5,441,955.
4-Azaisatin:

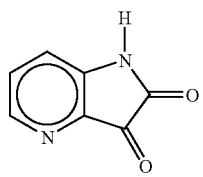

To a solution of 3-aminopicolinic acid (2 mmol, Hurd, C. D. et al. *J. Org. Chem.* 35:1471, 1970) and sodium carbonate (2.1 mmol) in water is added triphosgene (0.6 mmol). The reaction mixture is allowed to stir for 14 h at room temperature after which time the pH is adjusted to 3 and the resulting precipitate, 6-azaisatoic anhydride, is filtered.

Using the procedure in Synthesis 8 and substituting 6-azaisatoic anhydride for 5-azaisatoic anhydride, gives the title compound.

Synthesis 12 as Described in U.S. Pat. No. 5,441,955.
2-Chloro-8-fluoroindolo[2,1-b]quinazoline-6,12-dione:

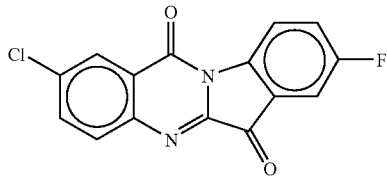

Isatoic anhydrides were prepared from 2-aminobenzoic acid derivatives using the following procedure. A solution of 2-amino-5-chlorobenzoic acid (1.56 g, 9.7 mmol) in 25 mL of dry THF and triphosgene (1.00 g, 3.3 mmol) was stirred at room temperature for 18 h. The resultant solid was filtered, washed with cold acetone, and dried under vacuum to give 1.56 g (89%) of 5-chloroisatoic anhydride.

To a suspension of NaH (10 mmol, 40 mg 60%) in 4 mL of DMF was added 10 mmol of 5-fluoroisatin in 2 mL of DMF. After 15 min, a solution of 5-chloroisatoic anhydride in 3 mL of DMF was added. The reaction mixture was stirred for 18 h, methanol (0.5 mL) and 20 mL of chloroform was added and the organic solution was washed with water, dried (MgSO$_4$) and concentrated to give a residue that was purified by silica gel chromatography (CHCl$_3$:CH$_3$OH). Yield 77%: mp 280-282° C.

Synthesis 13 as Described in U.S. Pat. No. 5,441,955.
3,8-Difluoroindolo[2,1-b]quinazoline-6,12-dione:

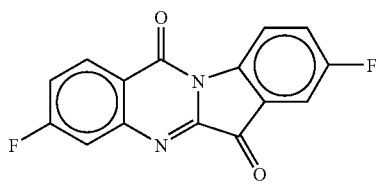

5-Fluoroisatin (2.20 g, 13.3 mmol) and 4-fluoroisatoic anhydride that was prepared according to the procedure in Synthesis 12 (2.64 g, 14.6 mmol) were dissolved in 130 mL of dry dimethylformamide (DMF), DBU (2.22 g, 14.6 mmol) and 4-dimethylaminopyridine (DMAP, 0.16 g, 1.33 mmol) were added over 2 min. The reaction was stirred for 19 h and 130 mL of 0.2 M HCl was added that produced a precipitate. The precipitate was filtered, washed with water (3×20 mL) and ethyl acetate (20 mL). The crude solid was purified by chromatography on silica gel eluting with chloroform giving the title compound in 20% yield: mp 297-298° C.; $^1$H NMR (300 MHz, CDCl$_3$) δ 8.64 (dd, 1H), 8.45 (dd, 1H), 7.69 (dd, 1H), 7.58 (dd, 1H), 7.5 (dt, 1H), 7.4 (dt, 1H).

Synthesis 14 as Described in U.S. Pat. No. 5,441,955.
10-Fluoroindolo[2,1-b]quinazoline-6,12-dione:

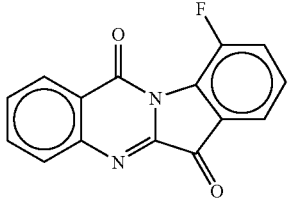

A solution of 7-fluoroisatin (300 mg, 1.8 mmol), isatoic anhydride (1.2 g, 7.3 mmol), and dimethylaminopyridine (222 mg, 2 mmol) in 5 mL of pyridine were heated at reflux temperature for 64 h. 50 mL of 0.2N HCl and 100 mL of chloroform were added and the chloroform layer was separated. The water layer was extracted with chloroform and the combined organic extracts were concentrated. Chromatography on silica gel eluting with chloroform gave the title compound in 14% yield: mp 264-267° C.; $^1$H NMR (300 MHz, CDCl$_3$) δ 8.46 (d, 1H) 8.02 (d, 1H) 7.82-7.92 (m, 1H) 7.79 (d, 1H) 7.64-7.74 (m, 1H) 7.52-7.64 (m, 1H) 7.40-7.49 (m, 1H).

Synthesis 15 as Described in U.S. Pat. No. 5,441,955.
6-Hydrobenzo[d]pyridino[2',3'-5,4]pyrimidino[1,2-a]azoline-5,11-dione:

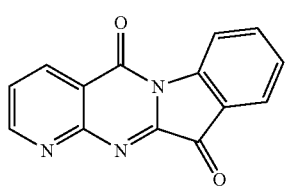

To a solution of 2-[1H-benzotriazole-1-yl]-1,1,3,3-tetramethyluronium hexafluorophosphate (HBTU, 2.85 g, 7.52 mmol), N-methylmorpholine (NMM, 1.5 mL, 13.7 mmol), and 2-aminonicotinic acid (1.04 g, 7.53 mmol) in 50 mL of dry DMF was added a solution of isatin (1.01 g, 6.83 mmol) and DBU (1,8-diazabicyclo[5.4.0]undec-7-ene, 2.5 mL, 16.7 mmol) in 40 mL dry DMF over 12 min at room temperature. After 20 hours, the reaction mixture was quenched with 200 mL of 1N citric acid solution. Water was added to make the final volume 1 L. The mixture was filtered to give 520 mg of residue. The filtrate was extracted with 5×100 mL of chloroform, washed with 2×300 mL of water. The organic layer was dried over anhydrous sodium sulfate, filtered and solvent removed in vacuo to give an oil. Silica gel chromatography purification of the oil and residue using (5:1) methylene chloride:ethyl acetate as eluent gave the title compound in 40% yield: mp 272° C. (dec) $^1$H NMR (DMSO-d$_6$) δ 7.48-7.56 (m, 1H) 7.727.78 (m, 1H) 7.86-7.96 (m, 2H) 8.43-8.48 (m, 1H) 8.68-8.74 (m, 1H), 9.05-9.10 (m, 1H). MS (MH+) 250.

Example 1

SMIPS

Candidate small molecule immune potentiators can be identified in vitro. Compounds are screened in vitro for their ability to stimulate human peripheral blood mononuclear cells to produce cytokines (e.g. TNF-a and IL-12 p40). Apoptosis inducing small molecules may be identified having this activity. These small molecule immunopotentiators have potential utility as adjuvants and immunotherapeutics.

In an assay procedure (High Throughput Screening (HTS)) for small molecule immune potentiators (SMIPs), human peripheral blood mononuclear cells (PBMC), 500,000 per mL in RPMI 1640 medium with 10% FCS, are distributed in 96 well plates (100,000 per well) already containing 5 μM of compound in DMSO. The PBMCs are incubated for 18 h at 37° C. in 5% CO$_2$. Their ability to produce cytokines in response to the small molecule compounds is determined using a modified sandwich ELISA.

Briefly supernatants from the PBMC cultures are assayed for secreted TNF using a primary plate bound antibody for capture followed by a secondary biotinylated anti-TNF antibody forming a sandwich. The biotinylated second antibody is then detected using streptavidin-Europium and the amount of bound europium is determined by time resolved fluorescence. Compounds are screened for their TNF inducing activity that is measured in the assay as increased Europim counts over cells incubated in RPMI medium alone. "Hits" are selected based on their TNF-inducing activity relative to an optimal dose of lipopolysaccaride LPS (1 μg/ml), a strong TNF inducer. The robustness of the assay and low backgrounds have allowed for the routine selection of hits with ~10% of LPS activity that is normally between 5-10× background (cells alone). Selected hits are then subjected to confirmation for their ability to induce cytokines from multiple donors at decreasing concentrations. Those compounds with consistent activity at or below 5 μM are considered confirmed for the purposes of this assay. The assay is readily modified for screening for compounds effective at higher or lower concentrations.

Example 2

Each of the compounds listed in Table 1, that may be synthesized as described herein and in U.S. Pat. No. 5,441, 955, was assayed as described above in Example 1. The results are also shown in Table 1, where each of these compounds displayed activity with respect to production of TNF-a. Many of these compounds showed activity at less than 5 μM with respect to production of TNF-a. Many of these compounds showed activity in the production of TNF-a at less than 1.5 μM.

In Table 1, the symbols +, ++, and +++ with respect to activity, by the assay of Example 1, refer to:
+++ active in the production of TNF-a at 1.5 μM or less;
++ active in the production of TNF-a at 5 μM or more; and
+ active in the production of TNF-a at 20 μM or more.

For this reason, each of the R groups of any of the compounds listed in Table 1 is preferred. Additionally, because of the excellent activity of each of the compounds, each of these compounds is individually preferred and is preferred as a member of a group that includes any or all of the other compounds and each compound is preferred in methods of modulating immunopotentiation and in methods of treating biological conditions associated therewith, for example to be used as a vaccine adjuvant. Each of the compounds is also preferred for use in preparation of medicaments for vaccine adjuvants, immunopotentiation, treating cancer, reducing tumor growth and in treating biological conditions mediated therefrom.

Other tryptanthrin compounds were screened and found to not be effective at a concentration of 20 μM or less using the assay of Example 1, and these are listed in Table 2. These compounds are also useful within the scope of the invention, since the invention is not meant to be limited to those compounds that are useful at a concentration of 20 μM or less. Compounds may be useful that cause production of TNF-a at higher concentrations, such as 100 μM, 200 μM or 300 μM in the assays described herein. For example Loxoribine causes useful production of TNF-a at 300 μM (see Pope et al Imnunostimulatory Compound 7-Allyl-8-Oxoguanosine (Loxoribine) Induces a Distinct Subset of Murine Cytokines Cellular Immunology 162: 333-339 (1995)).

While the invention has been described with respect to specific examples including presently preferred modes of carrying out the invention, those skilled in the art will appreciate that there are numerous variations and permutations of the above described systems and techniques that fall within the spirit and scope of the invention.

TABLE 1

| Compound No. | Structure | Name | LC/MS (mz) MH+ | Activity* |
|---|---|---|---|---|
| 1001 | [structure] | 8-nitroindolo[2,1-b]quinazoline-6,12-dione | 294.2 | +++ |

TABLE 1-continued

| Compound No. | Structure | Name | LC/MS (mz) MH+ | Activity* |
|---|---|---|---|---|
| 1002 | 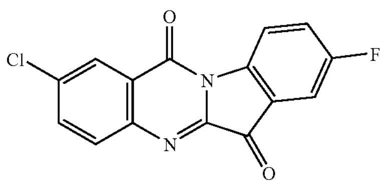 | 2-chloro-8-fluoroindolo[2,1-b]quinazoline-6,12-dione | 301.7 | ++ |
| 1003 | 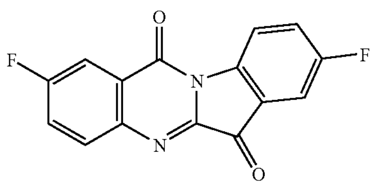 | 2,8-difluoroindolo[2,1-b]quinazoline-6,12-dione | 285.2 | ++ |
| 1004 | 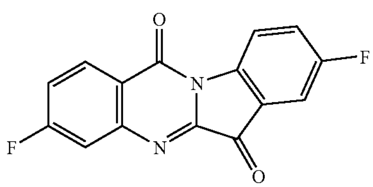 | 3,8-difluoroindolo[2,1-b]quinazoline-6,12-dione | 285.2 | +++ |
| 1005 | 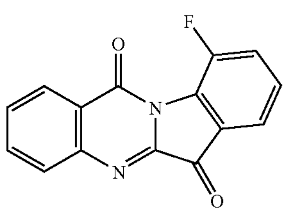 | 10-fluoroindolo[2,1-b]quinazoline-6,12-dione | 267.2 | +++ |
| 1006 | 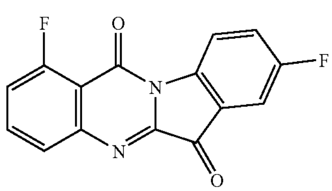 | 1,8-difluoroindolo[2,1-b]quinazoline-6,12-dione | 285.2 | +++ |
| 1007 | 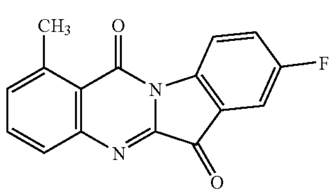 | 8-fluoro-1-methylindolo[2,1-b]quinazoline-6,12-dione | 281.3 | +++ |
| 1008 | 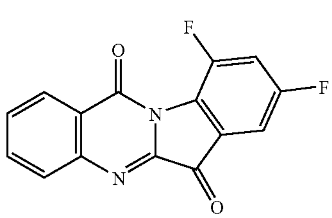 | 8,10-difluoroindolo[2,1-b]quinazoline-6,12-dione | 285.2 | +++ |

TABLE 1-continued

| Compound No. | Structure | Name | LC/MS (mz) MH+ | Activity* |
|---|---|---|---|---|
| 1009 | 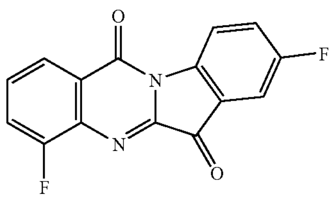 | 4,8-difluoroindolo[2,1-b]quinazoline-6,12-dione | 285.2 | ++ |
| 1010 | 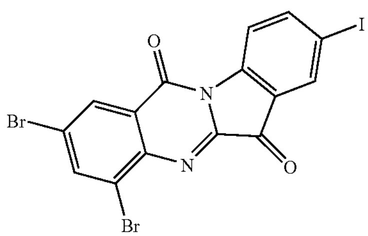 | 2,4-dibromo-8-iodoindolo[2,1-b]quinazoline-6,12-dione | 532.9 | ++ |
| 1011 | 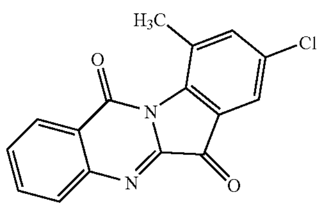 | 8-chloro-10-methylindolo[2,1-b]quinazoline-6,12-dione | 297.7 | ++ |
| 1012 | 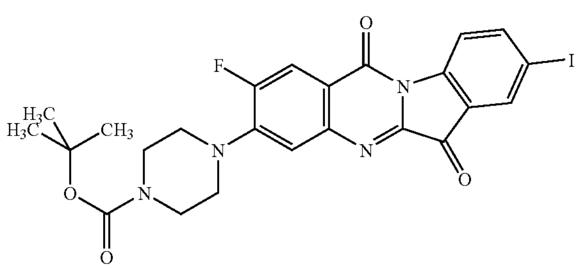 | 1,1-dimethylethyl 4-(2-fluoro-8-iodo-6,12-dioxo-6,12-dihydroindolo[2,1-b]quinazolin-3-yl)piperazine-1-carboxylate | 577.4 | ++ |
| 1013 | 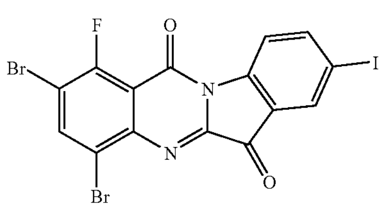 | 2,4-dibromo-1-fluoro-8-iodoindolo[2,1-b]quinazoline-6,12-dione | 550.9 | +++ |
| 1014 | 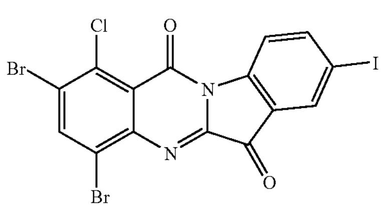 | 2,4-dibromo-1-chloro-8-iodoindolo[2,1-b]quinazoline-6,12-dione | 567.4 | +++ |
| 1015 | 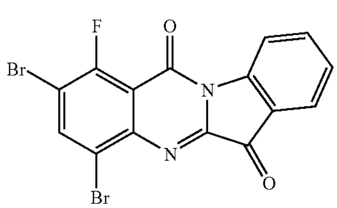 | 2,4-dibromo-1-fluoroindolo[2,1-b]quinazoline-6,12-dione | 425.0 | +++ |

TABLE 1-continued

| Compound No. | Structure | Name | LC/MS (mz) MH+ | Activity* |
|---|---|---|---|---|
| 1016 | 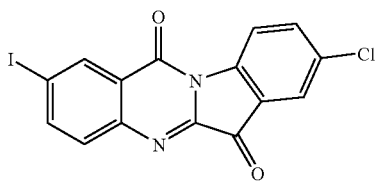 | 8-chloro-2-iodoindolo[2,1-b]quinazoline-6,12-dione | 409.6 | +++ |
| 1017 | 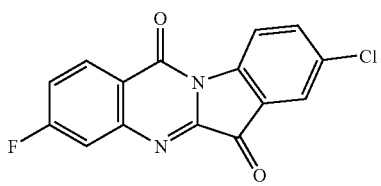 | 8-chloro-3-fluoroindolo[2,1-b]quinazoline-6,12-dione | 301.7 | +++ |
| 1018 | 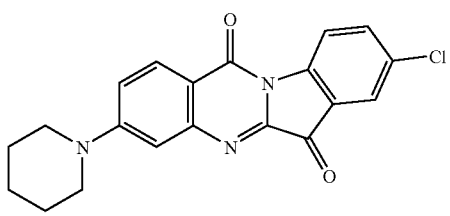 | 8-chloro-3-piperidin-1-ylindolo[2,1-b]quinazoline-6,12-dione | 366.8 | ++ |
| 1019 | 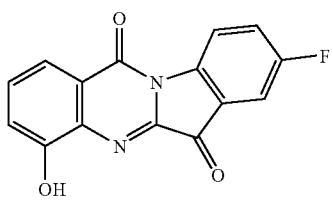 | 8-fluoro-4-hydroxyindolo[2,1-b]quinazoline-6,12-dione | 283.2 | +++ |
| 1020 | 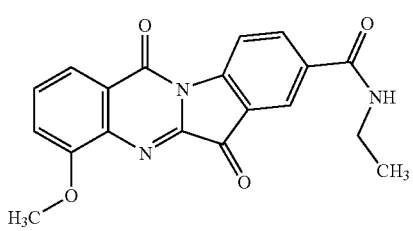 | N-ethyl-4-(methyloxy)-6,12-dioxo-6,12-dihydroindolo[2,1-b]quinazoline-8-carboxamide | 350.3 | +++ |
| 1021 | 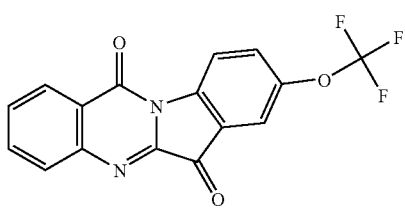 | 8-[(trifluoromethyl)oxy]indolo[2,1-b]quinazoline-6,12-dione | 333.2 | ++ |
| 1022 | 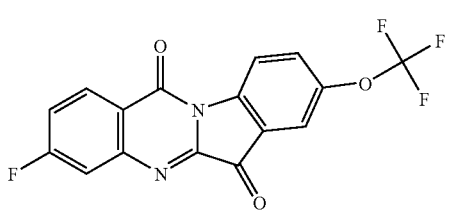 | 3-fluoro-8-[(trifluoromethyl)oxy]indolo[2,1-b]quinazoline-6,12-dione | 351.2 | +++ |

TABLE 1-continued

| Compound No. | Structure | Name | LC/MS (mz) MH+ | Activity* |
|---|---|---|---|---|
| 1023 | 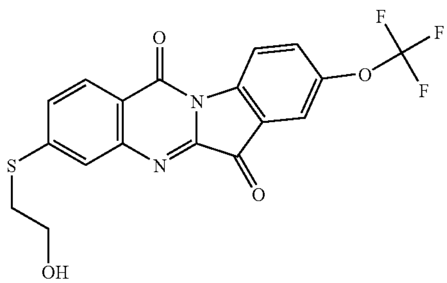 | 3-[(2-hydroxyethyl)thio]-8-[(trifluoromethyl)oxy]indolo[2,1-b]quinazoline-6,12-dione | 409.4 | +++ |
| 1024 | 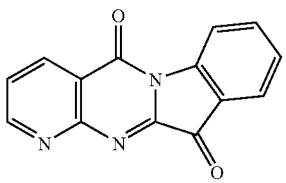 | pyrido[2',3':4,5]pyrimido[1,2-a]indole-5,11-dione | 250.2 | +++ |
| 1025 | 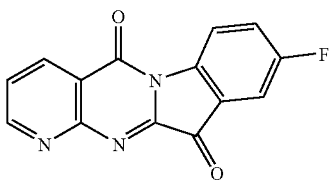 | 9-fluoropyrido[2',3':4,5]pyrimido[1,2-a]indole-5,11-dione | 268.2 | +++ |
| 1026 | 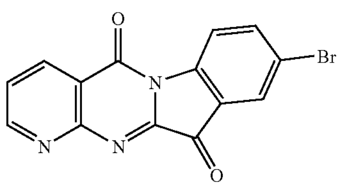 | 9-bromopyrido[2',3':4,5]pyrimido[1,2-a]indole-5,11-dione | 329.1 | +++ |
| 1027 | 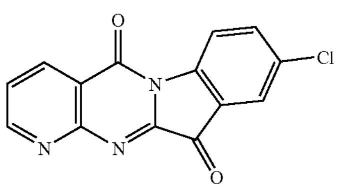 | 9-chloropyrido[2',3':4,5]pyrimido[1,2-a]indole-5,11-dione | 284.7 | +++ |
| 1028 | 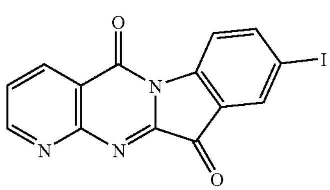 | 9-iodopyrido[2',3':4,5]pyrimido[1,2-a]indole-5,11-dione | 376.1 | +++ |
| 1029 | 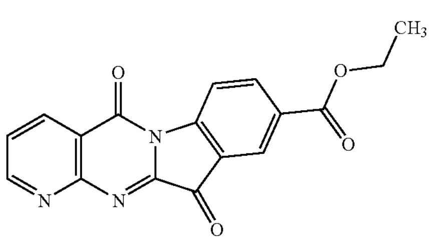 | ethyl 5,11-dioxo-5,11-dihydropyrido[2',3':4,5]pyrimido[1,2-a]indole-9-carboxylate | 322.3 | +++ |

TABLE 1-continued

| Compound No. | Structure | Name | LC/MS (mz) MH+ | Activity* |
|---|---|---|---|---|
| 1030 | 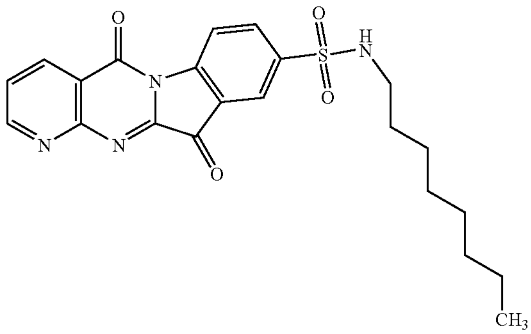 | N-octyl-5,11-dioxo-5,11-dihydropyrido[2',3':4,5]pyrimido[1,2-a]indole-9-sulfonamide | 441.5 | +++ |
| 1031 | 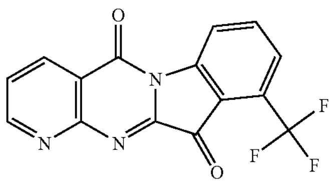 | 10-(trifluoromethyl)pyrido[2',3':4,5]pyrimido[1,2-a]indole-5,11-dione | 318.2 | +++ |
| 1032 | 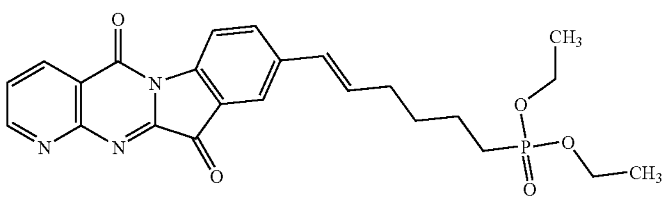 | diethyl (5E)-6-(5,11-dioxo-5,11-dihydropyrido[2',3':4,5]pyrimido[1,2-a]indol-9-yl)hex-5-enylphosphonate | 468.5 | ++ |
| 1033 | 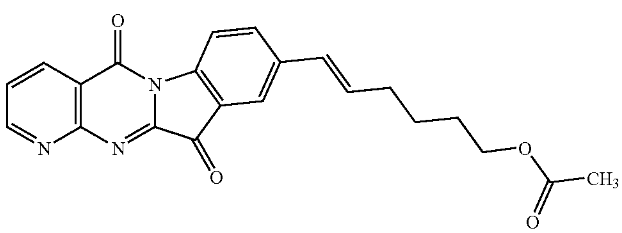 | (5E)-6-(5,11-dioxo-5,11-dihydropyrido[2',3':4,5]pyrimido[1,2-a]indol-9-yl)hex-5-enyl acetate | 390.4 | +++ |
| 1034 | 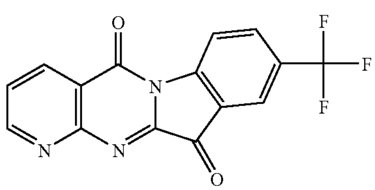 | 9-(trifluoromethyl)pyrido[2',3':4,5]pyrimido[1,2-a]indole-5,11-dione | 318.2 | ++ |
| 1035 | 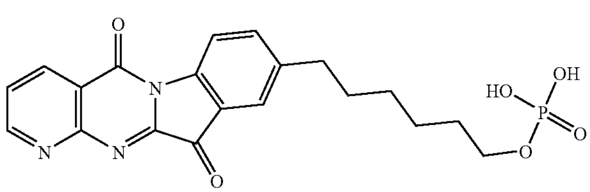 | 6-(5,11-dioxo-5,11-dihydropyrido[2',3':4,5]pyrimido[1,2-a]indol-9-yl)hexyl dihydrogen phosphate | 430.4 | +++ |
| 1036 | 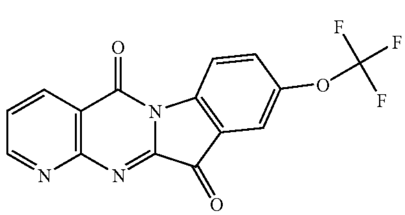 | 9-[(trifluoromethyl)oxy]pyrido[2',3':4,5]pyrimido[1,2-a]indole-5,11-dione | 334.2 | +++ |

TABLE 1-continued

| Compound No. | Structure | Name | LC/MS (mz) MH+ | Activity* |
|---|---|---|---|---|
| 1037 | 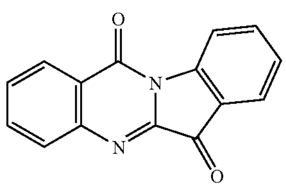 | indolo[2,1-b]quinazoline-6,12-dione | 249.2 | + |
| 1038 | 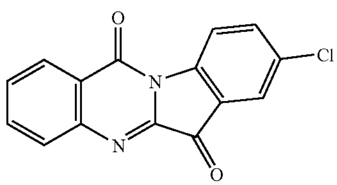 | 8-chloroindolo[2,1-b]quinazoline-6,12-dione | 283.7 | + |
| 1039 | 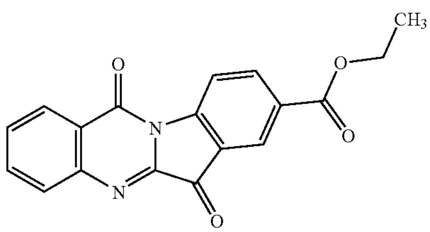 | ethyl 6,12-dioxo-6,12-dihydroindolo[2,1-b]quinazoline-8-carboxylate | 321.3 | + |
| 1040 | 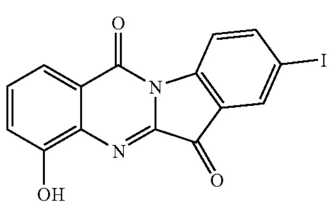 | 4-hydroxy-8-iodoindolo[2,1-b]quinazoline-6,12-dione | 391.1 | + |
| 1041 | 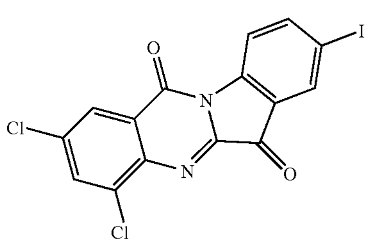 | 2,4-dichloro-8-iodoindolo[2,1-b]quinazoline-6,12-dione | 444.0 | + |
| 1042 | 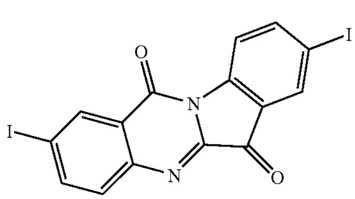 | 2,8-diiodoindolo[2,1-b]quinazoline-6,12-dione | 501.0 | + |
| 1043 | 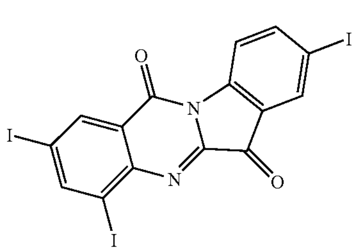 | 2,4,8-triiodoindolo[2,1-b]quinazoline-6,12-dione | 626.9 | + |

TABLE 1-continued

| Compound No. | Structure | Name | LC/MS (mz) MH+ | Activity* |
|---|---|---|---|---|
| 1044 | 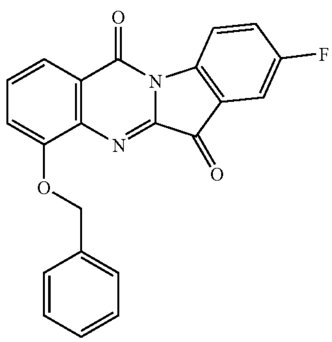 | 8-fluoro-4-[(phenylmethyl)oxy]indolo[2,1-b]quinazoline-6,12-dione | 373.4 | + |
| 1045 | 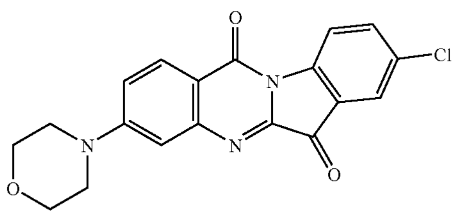 | 8-chloro-3-morpholin-4-ylindolo[2,1-b]quinazoline-6,12-dione | 368.8 | + |
| 1046 | 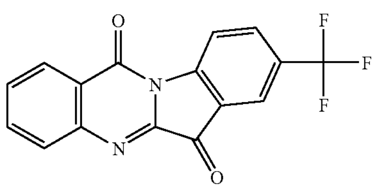 | 8-(trifluoromethyl)indolo[2,1-b]quinazoline-6,12-dione | 317.2 | + |
| 1047 | 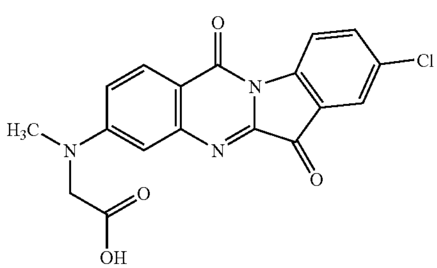 | [(8-chloro-6,12-dioxo-6,12-dihydroindolo[2,1-b]quinazolin-3-yl)(methyl)amino]acetic acid | 370.8 | + |
| 1048 | 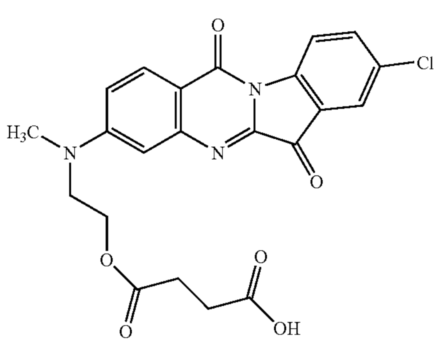 | 4-({2-[(8-chloro-6,12-dioxo-6,12-dihydroindolo[2,1-b]quinazolin-3-yl)(methyl)amino]ethyl}oxy)-4-oxobutanoic acid | 456.9 | + |

TABLE 1-continued

| Compound No. | Structure | Name | LC/MS (mz) MH+ | Activity* |
|---|---|---|---|---|
| 1049 | 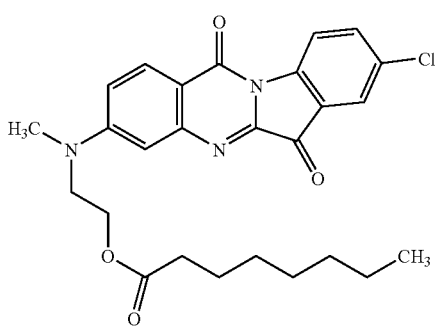 | 2-[(8-chloro-6,12-dioxo-6,12-dihydroindolo[2,1-b]quinazolin-3-yl)(methyl)amino]ethyl octanoate | 483.0 | + |
| 1050 | 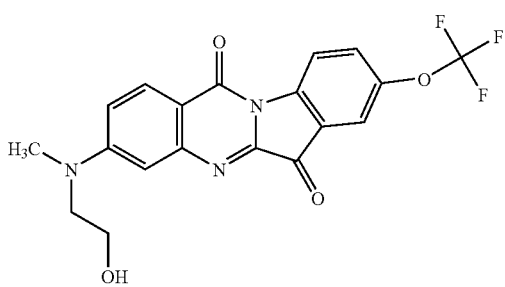 | 3-[(2-hydroxyethyl)(methyl)amino]-8-[(trifluoromethyl)oxy]indolo[2,1-b]quinazoline-6,12-dione | 406.3 | + |
| 1051 | 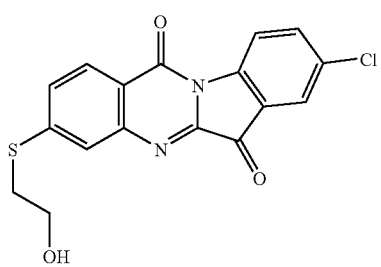 | 8-chloro-3-[(2-hydroxyethyl)thio]indolo[2,1-b]quinazoline-6,12-dione | 359.8 | + |
| 1052 | 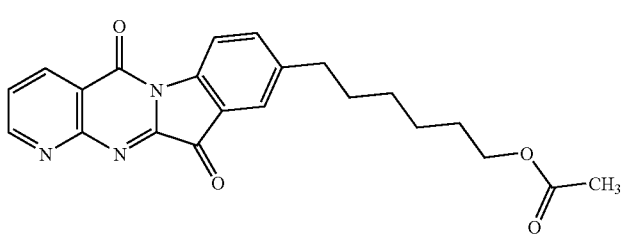 | 6-(5,11-dioxo-5,11-dihydropyrido[2',3':4,5]pyrimido[1,2-a]indol-9-yl)hexyl acetate | 392.4 | + |

TABLE 2

| Compound No. | Structure | Name | MH+ |
|---|---|---|---|
| 2001 | 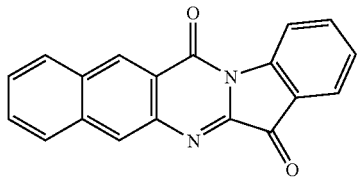 | benzo[g]indolo[2,1-b]quinazoline-6,14-dione | 299.3 |

TABLE 2-continued

| Compound No. | Structure | Name | MH+ |
|---|---|---|---|
| 2002 | 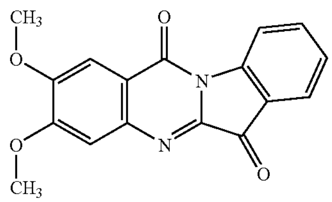 | 2,3-bis(methyloxy)indolo[2,1-b]quinazoline-6,12-dione | 309.3 |
| 2003 | 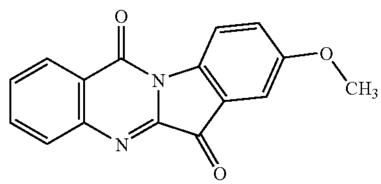 | 8(methyloxy)indolo[2,1-b]quinazoline-6,12-dione | 279.3 |
| 2004 | 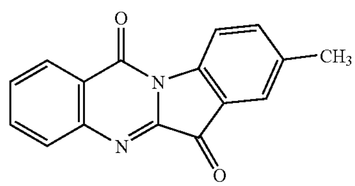 | 8-methylindolo[2,1-b]quinazoline-6,12-dione | 263.3 |
| 2005 | 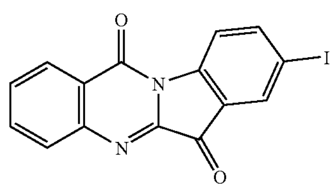 | 8-iodoindolo[2,1-b]quinazoline-6,12-dione | 375.1 |
| 2006 | 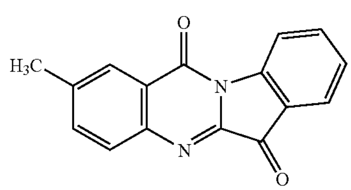 | 2-methylindolo[2,1-b]quinazoline-6,12-dione | 263.3 |
| 2007 | 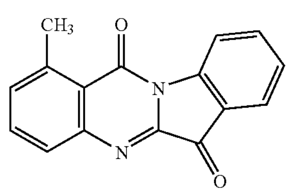 | 1-methylindolol[2,1-b]quinazoline-6,12-dione | 263.3 |
| 2008 | 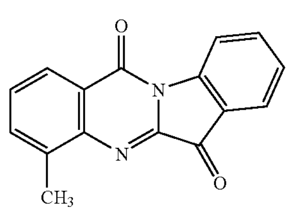 | 4-methylindolo[2,1-b]quinazoline-6,12-dione | 263.3 |

TABLE 2-continued

| Compound No. | Structure | Name | MH+ |
|---|---|---|---|
| 2009 | 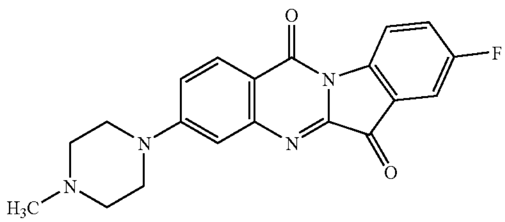 | 8-fluoro-3-(4-methylpiperazin-1-yl)indolo[2,1-b]quinazoline-6,12-dione | 365.4 |
| 2010 | 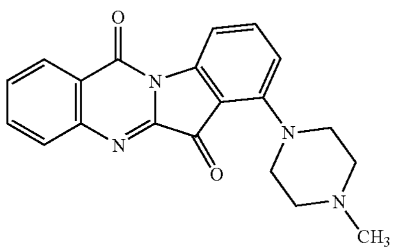 | 7-(4-methylpiperazin-1-yl)indolo[2,1-b]quinazoline-6,12-dione | 347.4 |
| 2011 | 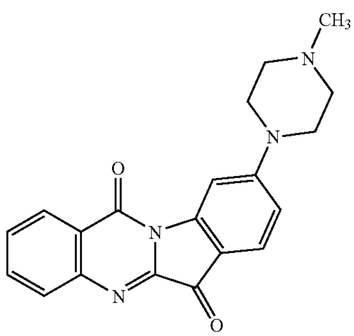 | 9-(4-methylpiperazin-1-yl)indolo[2,1-b]quinazoline-6,12-dione | 347.4 |
| 2012 | 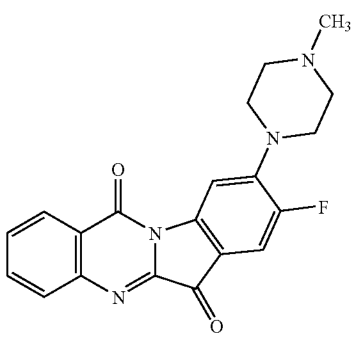 | 8-fluoro-9-(4-methylpiperazin-1-yl)indolo[2,1-b]quinazoline-6,12-dione | 365.4 |
| 2013 | 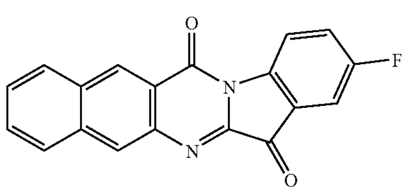 | 2-fluorobenzo[g]indolo[2,1-b]quinazoline-6,14-dione | 317.3 |
| 2014 | 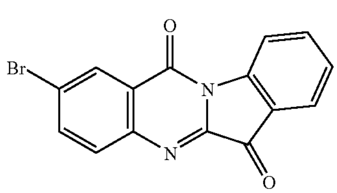 | 2-bromoindolo[2,1-b]quinazoline-6,12-dione | 328.1 |

TABLE 2-continued

| Compound No. | Name | MH+ |
|---|---|---|
| 2015 | 2-fluoroindolo[2,1-b]quinazoline-6,12-dione | 267.2 |
| 2016 | 2-amino-8-fluoroindolo[2,1-b]quinazoline-6,12-dione | 282.2 |
| 2017 | 9-chloroindolo[2,1-b]quinazoline-6,12-dione | 283.7 |
| 2018 | 7-chloroindolo[2,1-b]quinazoline-6,12-dione | 283.7 |
| 2019 | 8-fluoro-4-(methyloxy)indolo[2,1-b]quinazoline-6,12-dione | 297.3 |
| 2020 | 8-fluoro-2,4-dimethylindolo[2,1-b]quinazoline-6,12-dione | 295.3 |
| 2021 | 8-fluoro-2-methylindolo[2,1-b]quinazoline-6,12-dione | 281.3 |

TABLE 2-continued

| Compound No. | Structure | Name | MH+ |
|---|---|---|---|
| 2022 | 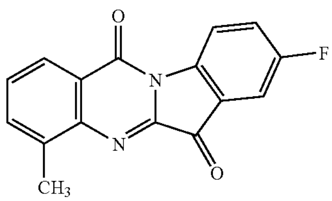 | 8-fluoro-4-methylindolo[2,1-b]quinazoline-6,12-dione | 281.3 |
| 2023 | 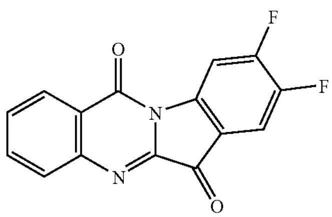 | 8,9-difluoroindolo[2,1-b]quinazoline-6,12-dione | 285.2 |
| 2024 | 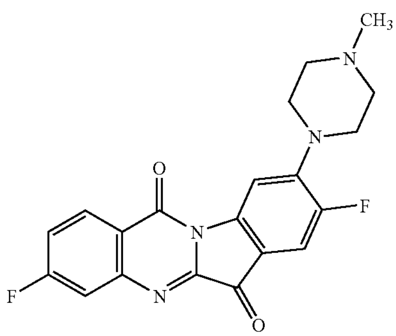 | 3,8-difluoro-9-(4-methylpiperazin-1-yl)indolo[2,1-b]quinazoline-6,12-dione | 383.4 |
| 2025 | 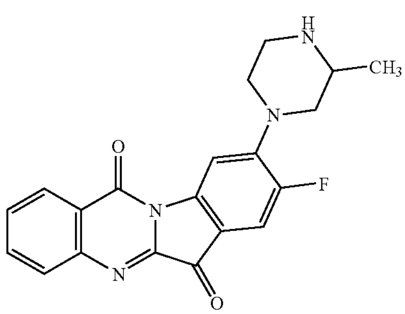 | 8-fluoro-9-(3-methylpiperazin-1-yl)indolo[2,1-b]quinazoline-6,12-dione | 365.4 |
| 2026 | 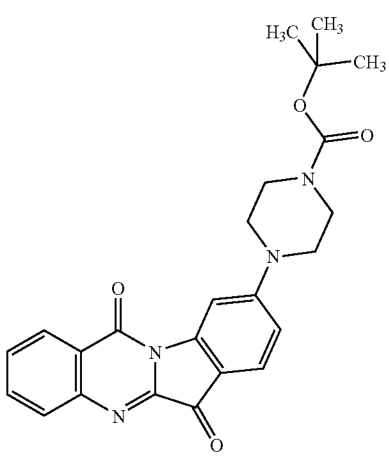 | 1,1-dimethylethyl 4-(6,12-dioxo-6,12-dihydroindolo[2,1-b]quinazolin-9-yl)piperazine-1-carboxylate | 433.5 |

TABLE 2-continued

| Compound No. | Structure | Name | MH+ |
|---|---|---|---|
| 2027 | 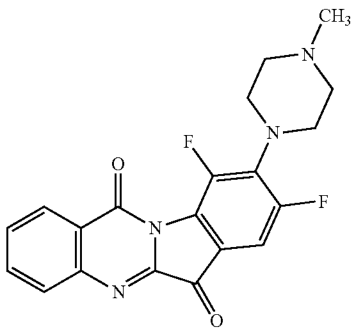 | 8,10-difluoro-9-(4-methylpiperazin-1-yl)indolo[2,1-b]quinazoline-6,12-dione | 383.4 |
| 2028 | 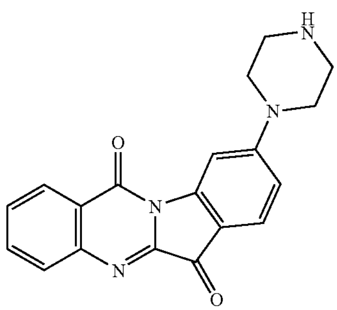 | 9-piperazin-1-ylindolo[2,1-b]quinazoline-6,12-dione | 333.4 |
| 2029 | 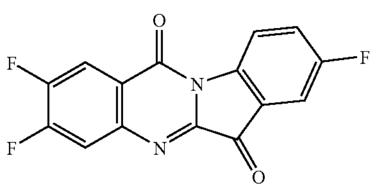 | 2,3,8-trifluoroindolo[2,1-b]quinazoline-6,12-dione | 303.2 |
| 2030 | 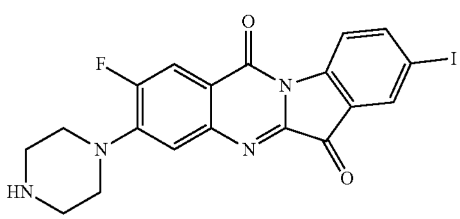 | 2-fluoro-8-iodo-3-piperazin-1-ylindolo[2,1-b]quinazoline-6,12-dione | 477.2 |
| 2031 | 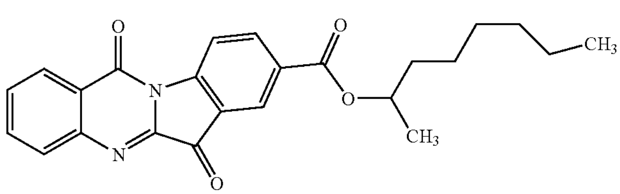 | 1-methylheptyl 6,12-dioxo-6,12-dihydroindolo[2,1-b]quinazoline-8-carboxylate | 405.5 |
| 2032 | 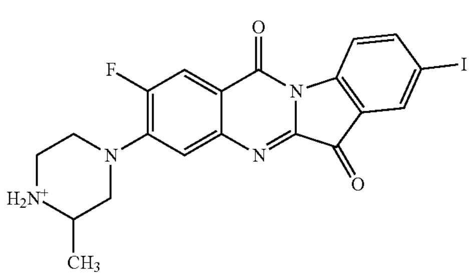 | 4-(2-fluoro-8-iodo-6,12-dioxo-6,12-dihydroindolo[2,1-b]quinazolin-3-yl)-2-methylpiperazin-1-ium | 492.3 |

TABLE 2-continued
| Compound No. | Structure | Name | MH+ |
|---|---|---|---|
| 2033 | 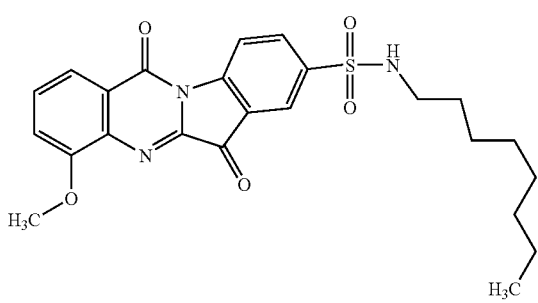 | 4-(methyloxy)-N-octyl-6,12-dioxo-6,12-dihydroindolo[2,1-b]quinazoline-8-sulfonamide | 470.6 |
| 2034 | 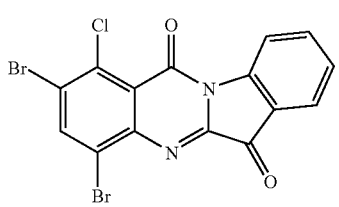 | 2,4-dibromo-1-chloroindolo[2,1-b]quinazoline-6,12-dione | 441.5 |
| 2035 | 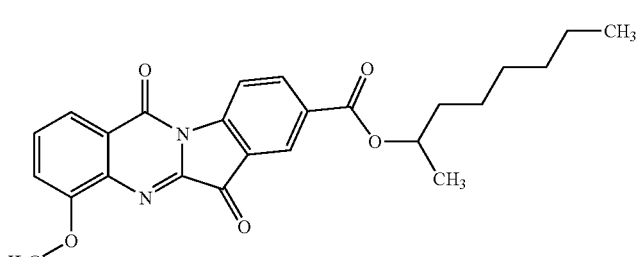 | 1-methylheptyl 4-(methyloxy)-6,12-dioxo-6,12-dihydroindolo[2,1-b]quinazoline-8-carboxylate | 435.5 |
| 2036 | 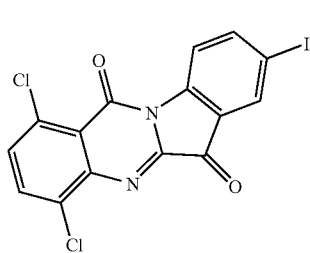 | 1,4-dichloro-8-iodoindolo[2,1-b]quinazoline-6,12-dione | 444.0 |
| 2037 | 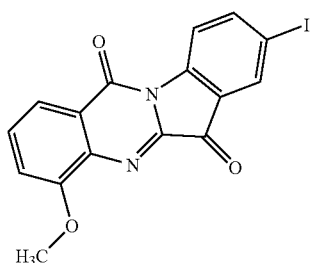 | 8-iodo-4-(methyloxy)indolo[2,1-b]quinazoline-6,12-dione | 405.2 |
| 2038 | 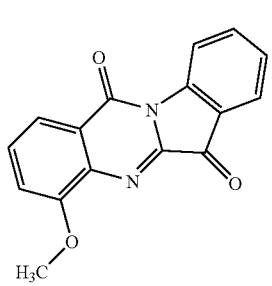 | 4-(methyloxy)indolo[2,1-b]quinazoline-6,12-dione | 279.3 |

TABLE 2-continued

| Compound No. | Structure | Name | MH+ |
|---|---|---|---|
| 2039 | 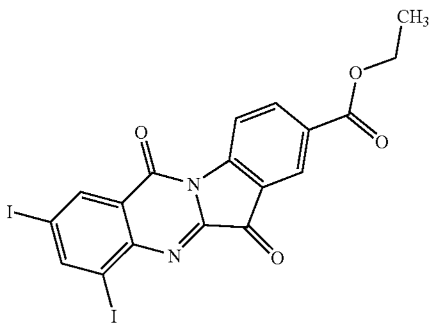 | ethyl 2,4-diiodo-6,12-dioxo-6,12-dihydroindolo[2,1-b]quinazoline-8-carboxylate | 573.1 |
| 2040 | 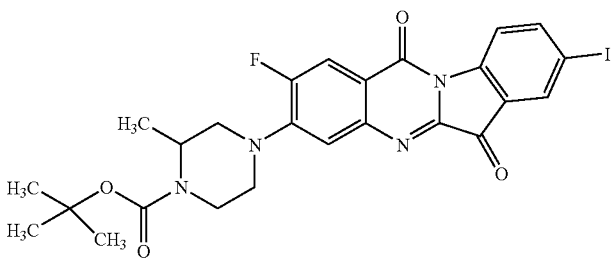 | 1,1-dimethylethyl 4-(2-fluoro-8-iodo-6,12-dioxo-6,12-dihydroindolo[2,1-b]quinazolin-3-yl)-2-methylpiperazine-1-carboxylate | 591.4 |
| 2041 | 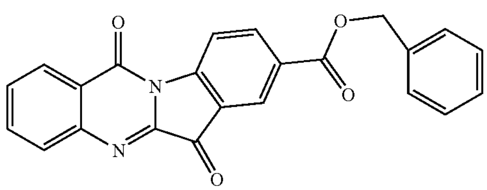 | phenylmethyl 6,12-dioxo-6,12-dihydroindolo[2,1-b]quinazoline-8-carboxylate | 383.4 |
| 2042 | 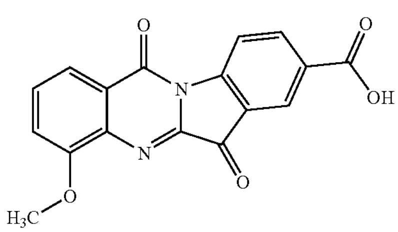 | 4-(methyloxy)-6,12-dioxo-6,12-dihydroindolo[2,1-b]quinazoline-8-carboxylic acid | 323.3 |
| 2043 | 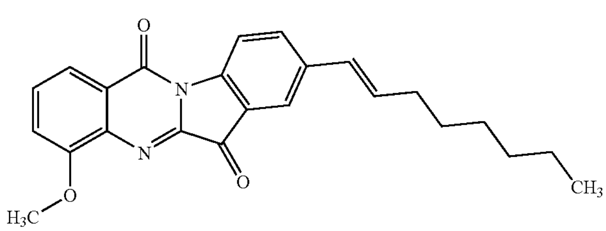 | 4-(methyloxy)-8-[(1E)-oct-1-enyl]indolo[2,1-b]quinazoline-6,12-dione | 389.5 |
| 2044 | 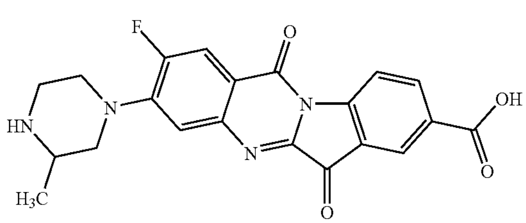 | 2-fluoro-3-(3-methylpiperazin-1-yl)-6,12-dioxo-6,12-dihydroindolo[2,1-b]quinazoline-8-carboxylic acid | 409.4 |

TABLE 2-continued

| Compound No. | Structure | Name | MH+ |
|---|---|---|---|
| 2045 | 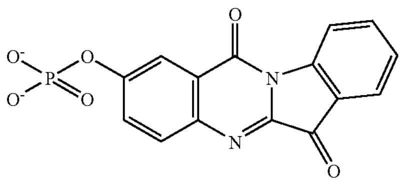 | 6,12-dioxo-6,12-dihydroindolo[2,1-b]quinazolin-2-ylphosphonic acid | 343.2 |
| 2046 | 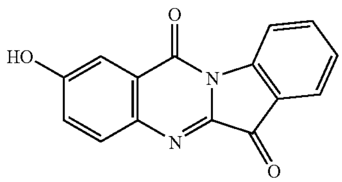 | 2-hydroxyindolo[2,1-b]quinazoline-6,12-dione | 265.2 |
| 2047 | 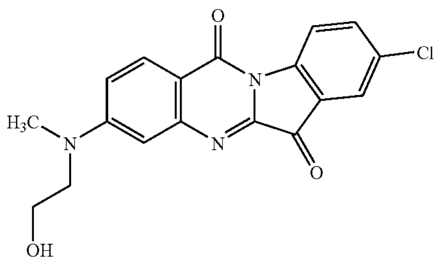 | 8-chloro-3-[(2-hydroxyethyl)(methyl)amino]indolo[2,1-b]quinazoline-6,12-dione | 356.8 |
| 2048 | 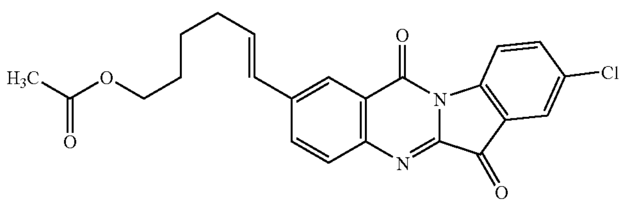 | (5E)-6-(8-chloro-6,12-dioxo-6,12-dihydroindolo[2,1-b]quinazolin-2-yl)hex-5-enyl acetate | 423.9 |
| 2049 | 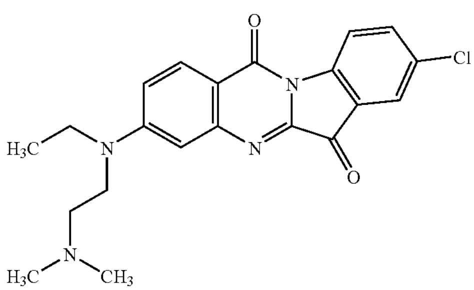 | 8-chloro-3-[[2-(dimethylamino)ethyl](ethyl)amino]indolo[2,1-b]quinazoline-6,12-dione | 397.9 |
| 2050 | 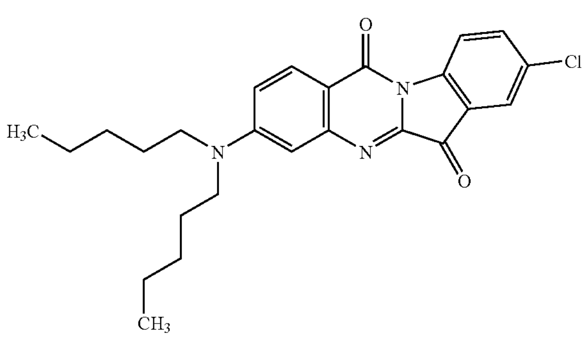 | 8-chloro-3-(dipentylamino)indolo[2,1-b]quinazoline-6,12-dione | 439.0 |

TABLE 2-continued

| Compound No. | Structure | Name | MH+ |
|---|---|---|---|
| 2051 | 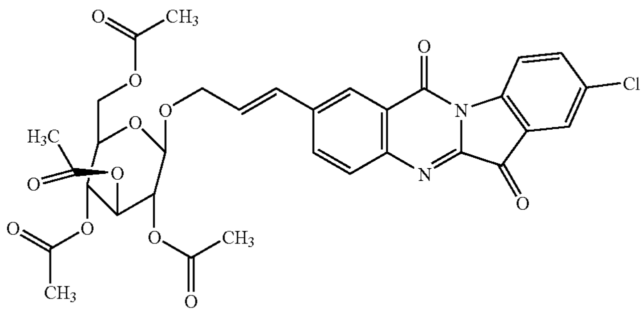 | (2E)-3-(8-chloro-6,12-dioxo-6,12-dihydroindolo[2,1-b]quinazolin-2-yl)prop-2-enyl 2,3,4,6-tetra-O-acetylhexopyranoside | 670.0 |
| 2052 | 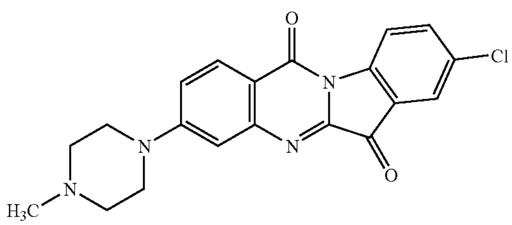 | 8-chloro-3-(4-methylpiperazin-1-yl)indolo[2,1-b]quinazoline-6,12-dione | 381.8 |
| 2053 | 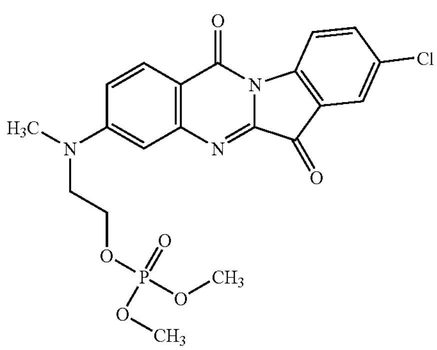 | 2-[(8-chloro-6,12-dioxo-6,12-dihydroindolo[2,1-b]quinazolin-3-yl)(methyl)amino]ethyl dimethyl phosphate | 464.8 |
| 2054 | 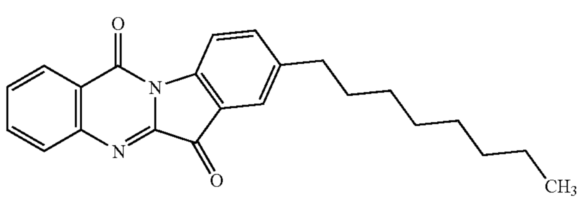 | 8-octylindolo[2,1-b]quinazoline-6,12-dione | 361.5 |
| 2055 | 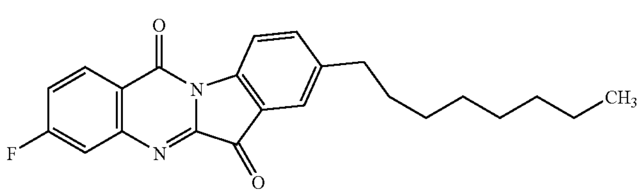 | 3-fluoro-8-octylindolo[2,1-b]quinazoline-6,12-dione | 379.4 |
| 2056 | 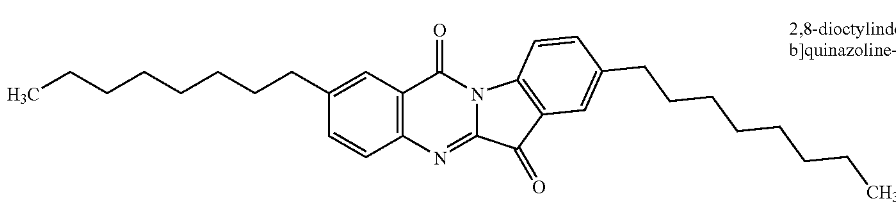 | 2,8-dioctylindolo[2,1-b]quinazoline-6,12-dione | 473.7 |

TABLE 2-continued

| Compound No. | Structure | Name | MH+ |
|---|---|---|---|
| 2057 | 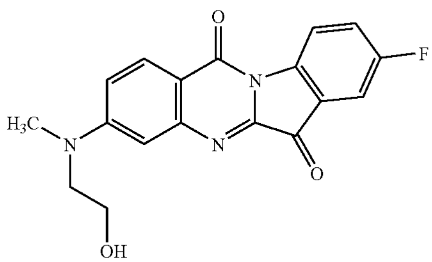 | 8-fluoro-3-[(2-hydroxyethyl)(methyl)amino]indolo[2,1-b]quinazoline-6,12-dione | 340.3 |
| 2058 | 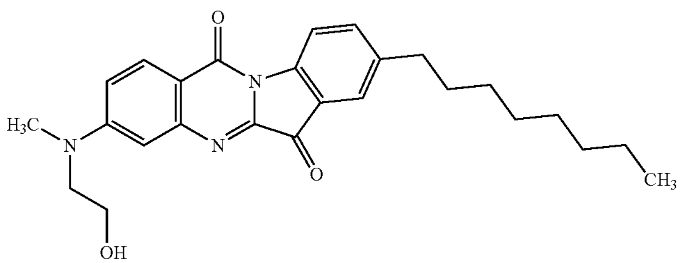 | 3-[(2-hydroxyethyl)(methyl)amino]-8-octylindolo[2,1-b]quinazoline-6,12-dione | 434.5 |
| 2059 | 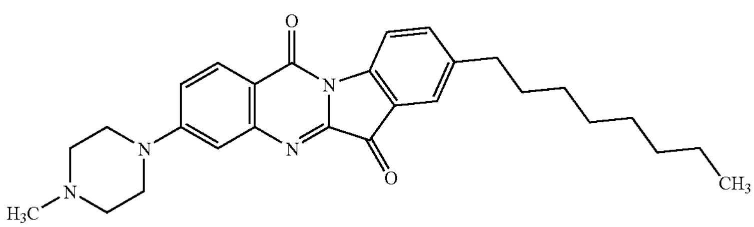 | 3-(4-methylpiperazin-1-yl)-8-octylindolo[2,1-b]quinazoline-6,12-dione | 459.6 |
| 2060 | 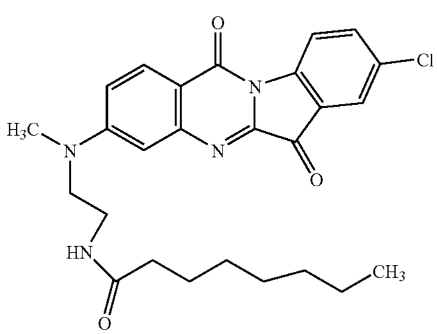 | N-{2-[(8-chloro-6,12-dioxo-6,12-dihydroindolo[2,1-b]quinazolin-3-yl)(methyl)amino]ethyl}octanamide | 482.0 |
| 2061 | 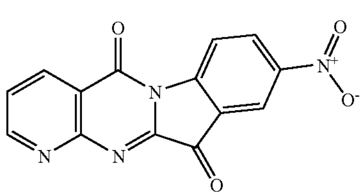 | 9-nitropyrido[2',3':4,5]pyrimido[1,2-a]indole-5,11-dione | 295.2 |
| 2062 | 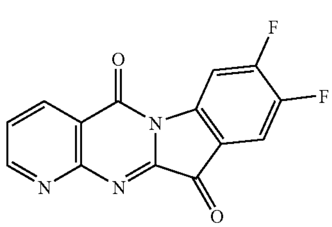 | 8,9-difluoropyrido[2',3':4,5]pyrimido[1,2-a]indole-5,11-dione | 286.2 |

TABLE 2-continued

| Compound No. | Structure | Name | MH+ |
|---|---|---|---|
| 2063 | 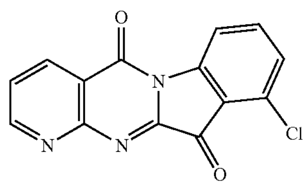 | 10-chloropyrido[2',3':4,5]pyrimido[1,2-a]indole-5,11-dione | 284.7 |
| 2064 | 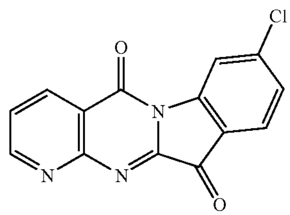 | 8-chloropyrido[2',3':4,5]pyrimido[1,2-a]indole-5,11-dione | 284.7 |

What is claimed is:

1. An immunogenic pharmaceutical composition comprising an antigen and a tryptanthrin compound adjuvant in an amount effective to provide an enhanced immune response to the antigen relative to the response provided without the tryptanthrin compound adjuvant.

2. The composition of claim 1, further comprising an aqueous carrier.

3. The composition of claim 1, wherein the antigen is associated with a disease selected from the group consisting of cholera, plague, typhoid, hepatitis B infection, influenza, inactivated polio, rabies, measles, mumps, rubella, oral polio, yellow fever, tetanus, diphtheria, *hemophilus influenzae* b, meningococcus infection, tick borne encephalitis, SARS, HCV, HIV, and pneumococcus infection.

4. The composition of claim 1, wherein the tryptanthrin compound enhances an immune response to the antigen and the immune response is the cellular production of one or more cytokines.

5. The composition of claim 1, wherein the tryptanthrin compound is a compound of Formula I:

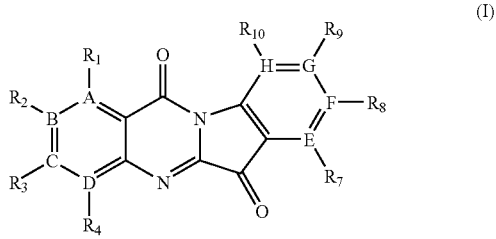

(I)

wherein
A, B, C, D, E, F, G, and H are independently selected from carbon and nitrogen, or A and B and/or C and D can be taken together to be nitrogen or sulfur;
$R_1, R_2, R_3, R_4, R_8,$ and $R_{10}$ are independently selected from the group consisting of hydrogen, halogen, loweralkyl, alkyl, substituted alkyl, cycloalkyl, heterocyclyl, alkylheterocyclyl, substituted heterocyclyl, substituted alkenyl, amino, (substituted alkyl)(alkyl)amino, imino, haloloweralkyl, hydroxy, alkoxy, substituted alkoxy, hydroxyalkylthio, nitro, alkylsulfonyl, N-alkylsulfonamide, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocyclyl, mercaptoalkoxyalkyl, cyano, formyl, —$COOR_{11}$ wherein $R_{11}$ is hydrogen, loweralkyl, aryl, heterocyclyl, monosaccharide or disaccharide, and —$CONR_{12}R_{13}$ wherein $R_{12}$ and $R_{13}$ are independently selected from hydrogen, loweralkyl, aryl, heterocyclyl, saccharide, peptide and amino acid residues; or $R_2$ and $R_3$ taken together form a six membered aromatic ring;
$R_7$ and $R_9$ are independently selected from hydrogen, halogen, loweralkyl, haloloweralkyl, cycloalkyl, heterocyclyl, substituted heterocyclyl or heterocyclylalkyl; and
$R_1, R_2, R_3, R_4, R_7, R_8, R_9,$ and $R_{10}$ are absent when the ring atom to which they would otherwise be bonded is sulfur or double-bonded nitrogen; or
a pharmaceutically acceptable salt thereof,
provided that $R_1, R_2, R_3, R_4, R_7, R_8, R_9,$ and $R_{10}$ are not all hydrogen when A, B, C, D, E, F, and H are carbon.

6. The composition of claim 5,
wherein
A, B, C, D, E, F, G, and H are independently selected from carbon and nitrogen;
$R_1, R_2, R_3, R_4, R_8$ and $R_{10}$ are independently selected from the group consisting of hydrogen, halogen, loweralkyl, alkyl, substituted alkyl, heterocyclyl, substituted heterocyclyl, substituted alkenyl, (substituted alkyl)(alkyl) amino, haloloweralkyl, hydroxy, alkoxy, substituted alkoxy, hydroxyalkylthio, nitro, N-alkylsulfonamide, cyano, —$COOR_{11}$ wherein $R_{11}$ is hydrogen, loweralkyl, aryl, heterocyclyl, monosaccharide or disaccharide, and —$CONR_{12}R_{13}$ wherein $R_{12}$ and $R_{13}$ are independently selected from hydrogen, loweralkyl, aryl, heterocyclyl, saccharide, peptide and amino acid residues.

7. The composition of claim 1, wherein the tryptanthrin compound is selected from the group consisting of
8-nitroindolo[2,1-b]quinazoline-6, 1-2-dione,
3,8-difluoroindolo[2,1-b]quinazoline-6,12-dione,
10-fluoroindolo[2,1-b]quinazoline-6,12-dione,
1,8-difluoroindolo[2,1-b]quinazoline-6,12-dione,
8-fluoro-1-methylindolo[2,1-b]quinazoline-6,12-dione,
8,10-difluoroindolo[2,1-b]quinazoline-6,12-dione, 2,4-dibromo-1-fluoro-8-iodoindolo[2,1-b]quinazoline-6,12-dione,
2,4-dibromo-1-chloro-8-iodoindolo[2,1-b]quinazoline-6,12-dione,
2,4-dibromo-1-fluoroindolo[2,1-b]quinazoline-6,12-dione,
8-chloro-2-iodoindolo[2,1-b]quinazoline-6,12-dione,
8-chloro-3-fluoroindolo[2,1-b]quinazoline-6,12-dione,
8-fluoro-4-hydroxyindolo[2,1-b]quinazoline-6,12-dione,
N-ethyl-4-(methyloxy)-6,12-dioxo-6,12-dihydroindolo[2,1-b]quinazoline-8-carboxamide,
3-fluoro-8-[(trifluoromethyl)oxy]indolo[2,1-b]quinazoline-6,12-dione,
3-[(2-hydroxyethyl)thio]-8-[(trifluoromethyl)oxy]indolo[2,1-b]quinazoline-6,12-dione,
pyrido[2',':4,5]pyrimido[1,2-a]indole-5,11-dione,
9-fluoropyrido[2',':4,5]pyrimido[1,2-a]indole-5,11-dione,
9-bromopyrido[2',':4,5]pyrimido[1,2-a]indole-5,11-dione,
9-chloropyrido[2',':4,5]pyrimido[1,2-a]indole-5,11-dione,
9-iodopyrido[2',':4,5]pyrimido[1,2-a]indole-5,11-dione,
ethyl 5,11-dioxo-5,11-dihydropyrido[2',':4,5]pyrimido[1,2-a]indole-9-carboxylate,
N-octyl-5,11-dioxo-5,11-dihydropyrido[2',':4,5]pyrimido[1,2-a]indole-9-sulfonamide,
10-(trifluoromethyl)pyrido[2',':4,5]pyrimido[1,2-a]indole-5,11-dione,
(5E)-6-(5,11-dioxo-5,11-dihydropyrido[2',':4,5]pyrimido[1,2-a]indol-9-yl)hex-5-enyl acetate,
6-(5,11-dioxo-5,11-dihydropyrido[2',':4,5]pyrimido[1,2-a]indol-9-yl)hexyl dihydrogen phosphate, and
9-[(trifluoromethyl)oxy]pyrido[2',':4,5]pyrimido[1,2-a]indole-5,11-dione,
or a pharmaceutically acceptable salt thereof.

* * * * *